US011857604B2

(12) United States Patent
Tillement et al.

(10) Patent No.: US 11,857,604 B2
(45) Date of Patent: Jan. 2, 2024

(54) NANOVECTORS AND USES

(71) Applicants: NH THERAGUIX, Meylan (FR); Universite Claude Bernard Lyon 1, Villeurbanne (FR); Centre National de La Recherche Scientifique—CNRS—, Paris (FR)

(72) Inventors: Olivier Tillement, Fontaines Saint-Martin (FR); François Lux, Lyons (FR); Fabien Rossetti, Villeurbanne (FR); Vu-Long Tran, Ho Chi Minh (VN); Clélia Mathieu, Bourg la Reine (FR); Myleva Dahan, Lyons (FR)

(73) Assignee: NH THERAGUIX, Meylan (FR)

( * ) Notice: Subject to any disclaimer, the term of this patent is extended or adjusted under 35 U.S.C. 154(b) by 492 days.

(21) Appl. No.: 16/755,866

(22) PCT Filed: Oct. 12, 2018

(86) PCT No.: PCT/FR2018/052538
§ 371 (c)(1),
(2) Date: Apr. 13, 2020

(87) PCT Pub. No.: WO2019/073182
PCT Pub. Date: Apr. 18, 2019

(65) Prior Publication Data
US 2020/0289623 A1 Sep. 17, 2020

(30) Foreign Application Priority Data
Oct. 13, 2017 (FR) ...................................... 1759607

(51) Int. Cl.
*A61K 38/31* (2006.01)
*A61K 47/69* (2017.01)
*A61P 35/00* (2006.01)
*A61K 33/243* (2019.01)
*A61K 9/14* (2006.01)
*A61K 31/704* (2006.01)
*A61K 49/00* (2006.01)
*A61K 49/12* (2006.01)
*A61K 49/18* (2006.01)
*B82Y 5/00* (2011.01)
*A61K 33/244* (2019.01)
*A61K 9/00* (2006.01)

(52) U.S. Cl.
CPC .............. *A61K 38/31* (2013.01); *A61K 9/146* (2013.01); *A61K 31/704* (2013.01); *A61K 33/243* (2019.01); *A61K 33/244* (2019.01); *A61K 47/6929* (2017.08); *A61K 49/0002* (2013.01); *A61K 49/128* (2013.01); *A61K 49/1881* (2013.01); *A61P 35/00* (2018.01); *B82Y 5/00* (2013.01); *A61K 9/0019* (2013.01)

(58) Field of Classification Search
CPC ...... A61K 38/31; A61K 9/146; A61K 31/704; A61K 33/243; A61K 33/244; A61K 47/6929; A61K 49/0002; A61K 49/128; A61K 49/1881; A61K 9/0019; A61K 31/00; A61K 9/08; A61K 41/0038; A61K 47/6935; A61P 35/00; B82Y 5/00; B82Y 15/00
See application file for complete search history.

(56) References Cited

U.S. PATENT DOCUMENTS

| 2004/0208822 A1 | 10/2004 | Madelmont et al. |
| 2006/0173160 A1 | 8/2006 | Dumy et al. |
| 2013/0195766 A1* | 8/2013 | Lux ................... A61K 49/0093 424/490 |
| 2020/0108155 A1 | 4/2020 | Cremillieux et al. |

FOREIGN PATENT DOCUMENTS

| WO | WO 01/00621 | 1/2001 |
| WO | WO 2004/026894 | 4/2004 |
| WO | WO 2011/135101 | 11/2011 |
| WO | WO 2013/153197 | 10/2013 |

OTHER PUBLICATIONS

Zamani, Gd (III) ion selective sensor, Mat. Sci. Eng. p. 717, Jan. (Year: 2012).*
Zamani, Gadolinium selective sensor, Mat. Sci. p. 488, July (Year: 2014).*
Tissier, Lasalocid, J. Chem. SOC., Faraday Trans. I, p. 1337, May (Year: 1989).*
Ganjali, Novel Gd(III) Sensor, Electroanaly. p. 2032, June (Year: 2005).*
Le Duc, G. et al., "Advantages of gadolinium based ultrasmall nanoparticles vs molecular gadolinium chelates for radiotherapy guided by MRI for glioma treatment," *Cancer Nanotechnology*, 5(4):1-14 (2014).
Maurin, M. et al., "Active targeting with Y-90 radiolabelled octreotate functionalized AGuIX ultra-small nano particles," *Nuclear Medicine and Biology*, 41(7):645 (2014); Abstract, Section 118.
Rocca, J.D. et al., "Polysilsesquioxane Nanoparticles for Targeted Platin-Based Cancer Chemotherapy by Triggered Release," *Angew. Chem. Int. Ed.*, 50:10330-4 (2011).
Zhang, Q. et al., "A surface-grafted ligand functionalization strategy for coordinate binding of doxorubicin at surface of PEGylated mesoporous silica nanoparticles: Toward pH-responsive drug delivery," *Colloids and Surfaces B: Biointerfaces*, 149:138-145 (2017).

(Continued)

*Primary Examiner* — David J Blanchard
*Assistant Examiner* — Thurman Wheeler
(74) *Attorney, Agent, or Firm* — Hoxie & Associates LLC

(57) ABSTRACT

The present invention relates to the field of nanovectors for the delivery of active substances in the body, in particular for the treatment of tumours. In particular, the use of these nanovectors makes it possible to improve the pharmacokinetics of the active substances with a more selective delivery, for example in the tumour tissues.

24 Claims, 10 Drawing Sheets

(56) References Cited

OTHER PUBLICATIONS

Anselmo et al., "An Overview of Clinical and Commercial Impact of Drug Delivery Systems," *J Control Release*, 190:15-28; pp. 1-35 (2014).
Anselmo et al., "Nanoparticles in the clinic," *Bioengineering & Translational Medicine*, 1:10-29 (2016).
Bazzi et al., "Synthesis and properties of europium-based phosphors on the nanometer scale: Eu2O3, Gd2O3:Eu, and Y2O3:Eu,," Journal of Colloid and Interface Science, 273(1):191-197 (2004); Abstract.
Bianchi et al., "Enhancement of anammox by the excretion of diel vertical migrators," PNAS, 111(44):15653-15658 (2014).
Bridot et al., "Hybrid Gadolinium Oxide Nanoparticles: Multimodal Contrast Agents for in Vivo Imaging," *J. Am. Chem. Soc.*, 129(16):5076-5084 (2007); Abstract.
Detappe et al., "Ultrasmall Silica-Based Bismuth Gadolinium Nanoparticles for Dual Magnetic Resonance-Computed Tomography Image Guided Radiation Therapy," *Nano Lett.*, 17(3): 1733-1740 (2017); Abstract.
Dufort et al., "Nebulized Gadolinium-Based Nanoparticles: A Theranostic Approach for Lung Tumor Imaging and Radiosensitization," Small, 11(2):215-221; Abstract.
Ji et al., "Antibacterial applications of graphene-based nanomaterials: Recent achievements and challenge, " *Adv Drug Deliv Rev*, 105(Pt B):176-189 (2016); Abstract.
Louis et al., "Nanosized Hybrid Particles with Double Luminescence for Biological Labeling," *Chem. Mater.*, 17(7):1673-1682 (2005); Abstract.
Lu et al., "Size Effect on Cell Uptake in Well-Suspended, Uniform Mesoporous Silica Nanoparticles," *Small*, 5(12):1408-13 (2009); Abstract.
Maier-Hauff et al., "Efficacy and safety of intratumoral thermotherapy using magnetic iron-oxide nanoparticles combined with external beam radiotherapy on patients with recurrent glioblastoma multiforme," *J Neurooncol*, 103:317-324 (2011).
Manzoor et al., "Overcoming Limitations in Nanoparticle Drug Delivery: Triggered, Intravascular Release to Improve Drug Penetration into Tumors," *Cancer Res*, 72(21):5566-5575 (2012).
Martini et al., "How Gold Particles Suppress Concentration Quenching of Fluorophores Encapsulated in Silica Beads," *J. Phys. Chem. C*, 113(41):17669-17677 (2009); Abstract.
Mignot et al., "A Top-Down Synthesis Route to Ultrasmall Multifunctional Gd-Based Silica Nanoparticles for Theranostic Applications," *Chem. Eur. J.*, 19:6122-6136 (2013).
Mphil et al., "Advances in silica based nanoparticles for targeted cancer therapy," *Nanomedicine: Nanotechnology, Biology and Medicine*, 12(2):317-332 (2016); Abstract.
Petersen et al., "Meta-analysis of clinical and preclinical studies comparing the anticancer efficacy of liposomal versus conventional non-liposomal doxorubicin," *J Control Release*, 232:255-64 (2016); Abstract.
Popović et al., "A Nanoparticle Size Series for In Vivo Fluorescence Imaging," *Angew Chem Int Ed Engl.*, 49(46): 8649-8652 (2010); Abstract.
Schütz et al., "Therapeutic nanoparticles in clinics and under clinical evaluation," *Nanomedicine*, 8(3): 1-19 (2013).
Shi et al., "Cancer nanomedicine: progress, challenges and opportunities," *Nat Rev Cancer*, 17(1):20-37; pp. 1-40; Author Manuscript (2017).
Stern et al., "Initial Evaluation of the Safety of Nanoshell-Directed Photothermal Therapy in the Treatment of Prostate Disease," *International Journal of Toxicology*, vol. 35(1): 38-46 (2016).
Vallet-Regí et al., "A New Property of MCM-41: Drug Delivery System," *Chem. Mater*, 13(2):308-311 (2001); Abstract.
Verry et al., "MRI-guided clinical 6-MV radiosensitization of glioma using a unique gadolinium-based nanoparticles injection," *Nanomedicine*, 11(18):2405-17 (2016); Abstract.

* cited by examiner

NANOVECTORS AND USES

CROSS REFERENCE TO RELATED APPLICATIONS

This application is a United States Application under 35 U.S.C. 371 claiming benefit of PCT Application No. PCT/FR2018/052538, filed on Oct. 12, 2018, which claims the benefit of French Patent Application No. 1759607, filed on Oct. 13, 2017, the contents of each of which are incorporated herein by reference.

TECHNICAL FIELD

The present invention relates to the field of nanovectors for delivering active substances in the body, in particular for the treatment of tumours. In particular, the use of these nanovectors makes it possible to improve the pharmacokinetics of the active substances with more selective delivery, for example into the tumour tissues.

CONTEXT

Since the arrival on the market of the first commercial nanoparticle in 1990 (Adagen®, Sigma-Tau Pharmaceuticals, Inc., MD, USA), a large number of research studies have been carried out for using nanoparticles for biomedical purposes (C. A. Schültz et al., *Nanomedicine,* 2013). Among these nanosystems, more than 20% of them are dedicated to the treatment of cancer by virtue of drug delivery. The use of nanoparticles for drug delivery in fact has a certain number of advantages over the direct intravenous injection of free chemotherapy: (i) increase in the solubility of the drug, (ii) improvement in the pharmacokinetics, (iii) prolonged half-life time in the blood stream (45 hours for Doxil® compared with 10 hours for free doxorubicin) (A. C. Anselmo et al., *Journal of Controlled Release,* 2015), (iv) minimization of side effects linked to delivery in non-targeted organs (Q. Qu et al., *Advanced Drug Delivery Reviews,* 2016).

To the knowledge of the inventors, at the current time, the vast majority of systems encapsulating an anticancer drug that has been approved at the regulatory level are based on pegylated or non-pegylated liposomes (except for Abraxane® which is alubumin based) (A. C. Anselmo, *Bioengineering & Translational Medicine,* 2016) (Table 1).

TABLE 1

Nanoparticles approved for cancerology

| Name | Particle type | Approved indications | Year of approval |
|---|---|---|---|
| Doxil ®/Caelyx ® (Janssen) | Pegylated liposome (doxorubicin) | Ovarian cancer; AIDS-associated Kaposi's sarcoma, myelomas, etc. | FDA (1995) EMA (1996) |
| DaunoXome ® (Galen) | Non-pegylated liposome (daunorubicin) | AIDS-associated Kaposi's sarcoma | FDA (1996) |
| Myocet ® (Teva UK) | Non-pegylated liposome | Metastatic breast cancer | EMA (2000) |
| Abraxane ® (Celgene) | Albumin (paclitaxel) | Non-small cell lung cancer | FDA (2005) EMA (2008) |
| Marquibo ® (Spectrum) | Non-pegylated liposome (vincristine) | Leukaemia | FDA (2012) |
| MEPACT ® (Millenium) | Non-pegylated liposome (mifamurtide) | Osteosarcoma | EMA (2009) |
| Onivyde MM-398 ® (Merrimack) | Pegylated liposome (irinotecan) | Metastatic pancreatic cancer | FDA (2015) |

Despite these few successes, the number of nanosystems in clinical use is low compared with the research efforts that have been dedicated to said nanosystems. Recent studies have shown that, even though formulations of doxorubicin encapsulated in liposomes have shown themselves to be effective in animals, they struggle to show a clinical benefit to human beings (G. H. Petersen et al., *Journal of Controlled Release,* 2016).

In addition to these difficulties in showing an efficacy in human beings, these systems generally prove to be complex from a chemical point of view, which makes them expensive to synthesize and difficult to transpose to the industrial scale (J. Shi et al., *Nature Reviews Cancer,* 2017). New studies lead to the idea that many nanosystems are too large to allow efficient extravasation in the tumour. Thus, even for liposomes which have a hydrodynamic diameter of around 100 nm, the penetration into the tumour is limited to a few cell layers starting from the blood vessel (A. A. Manzoor et al., *Cancer Research,* 2012). This limitation, combined with a relatively slow release of the active substances from the nanoparticle, can make it difficult to deliver active substances at an efficacious concentration.

In parallel to the work done on organic nanoparticles, inorganic nanoparticles have also been developed. With the exception of iron oxides for IRM (Endorem®, GastroMARK™, Resovist®, etc.), none had however yet reached the market in 2013 (C. A. Schültz et al., *Nanomedicine,* 2013), often for reasons of potential toxicity. One of the reasons for developing inorganic nanoparticles for biomedical applications is to take advantage of the properties that can emerge on the nanoscale: magnetic hyperthermia for iron oxides (Nanotherm®) (K. Maier-Hauff et al., Journal of Neurooncology, 2011), optical hyperthermia for gold nanoparticles (AuroShell®) (J. M. Stern et al., *International Journal of Toxicology,* 2016), etc.

In parallel to these applications, porous inorganic nanosystems have been developed for drug delivery. Among these porous systems, many developments have taken place on mesoporous silica nanoparticles, which were proposed for applications in oncology at the beginning of the 2000s (M. Vallet-Regi et al., *Chem. Mater.,* 2001) because of their good biocompatibility and their low cytotoxicity. The pores of these nanoparticles can be obtained between 2 and 50 nm for objects having sizes ranging from 10 nm to one micron (Y. Yang, *Nanomedicine: NBM,* 2016) for specific surface areas of between 200 and 1000 $m^2 \cdot g^{-1}$. Nevertheless, it should be noted that mesoporous silica nanoparticles which have a size of less than 50 nm remain difficult to synthesize and have a tendency to aggregate (F. Lu et al., *Small,* 2009).

In order to increase the extravasation and the tumour penetration, decreasing the size of the nanosystems is therefore increasingly emphasized by researchers (Z. Popovic et al., *Angew. Chem. Int. Ed.,* 2010). However, a decrease in size of the nanoparticles below 10 nm prevents the synthesis of stable porous structures.

At the current time, there is still therefore a need to develop new nanovectors for the delivery of active substances, and which would exhibit one or more of the following advantages:
- a very high surface/volume ratio favourable to a high degree of active substance load content,
- rapid nanovector elimination in the kidneys, limiting the toxicity problems,
- deep extravasation and penetration in tumours after administration for the treatment of tumours with the active substances,
- rapid and efficient in vivo release of the active substances,
- a possibility of monitoring the nanovectors after in vivo administration by imaging (MIR, scans or scintigraphy),
- a possibility of carrying out a complementary curative action by radiotherapy by virtue of the radiosensitizing aspect of high-Z metal chelates combined within one and the same nano-object. The combined action of chemotherapy and radiotherapy possibly making it possible to overcome the radio resistance of multiresistant cells.

These advantages and many others are obtained by means of the nanovectors described in the present disclosure.

DETAILED DESCRIPTION

In this context, the inventors have in fact noted that it is possible to use the recent strategies of synthesis of stable nanoparticles of polysiloxane having a hydrodynamic diameter of less than 5 nm (for example, F. Lux et al., *Angewandte Chemistry International Edition*, 2010) with a view to developing new nanovectors for drug delivery, said nanovectors being loaded by simple physisorption of the active substances at the surface of the polysiloxane-based ultrafine nanoparticles. The high surface/volume ratio of these ultrafine nanoparticles makes it possible to obtain a high degree of active surface load content for the nanovectors.

In one advantageous embodiment, the nanoparticles also have metal chelates at their surface, giving them a multimodality, in particular as a contrast or radiosensitizing agent.

The present disclosure thus relates to a method for preparing a nanovector for the delivery of active substances in human beings or animals, said method comprising mixing two solutions that can be administered in human beings or animals:
- a first solution comprising nanoparticles, said nanoparticles being chosen from polysiloxane-based nanoparticles having a mean diameter of less than 10 nm, preferably less than 5 nm, and
- a second solution comprising an active substance or a mixture of active substances chosen from organic molecules, preferably having a molecular weight of between 2% and 40% of the molecular weight of said nanoparticle, preferably between 5% and 25% of the molecular weight of said nanoparticle, under concentration ratio, pH and temperature conditions which allow an interaction by physisorption of the active substances at the surface of said nanoparticles.

For the purposes of the invention, the term "nanovector" denotes a particulate pharmaceutical system characterized by:
- a biocompatible structure (which does not induce toxic reactions),
- easy elimination from the organism,
- an active substance load, in order to ensure the transportation and the release of said active substances, preferentially at a biological target,
- a size of less than 100 nm.

The term "nanovector" according to the present disclosure denotes the nanovector with its active substance load.

The Nanoparticles that can be Used in the Preparation of the Nanovectors

The nanoparticles that can be used in the preparation of the nanovectors comprise two essential characteristics:
- they are polysiloxane based,
- they have a very small mean diameter, for example a hydrodynamic diameter of less than 10 nm, preferably less than 5 nm.

For the purposes of the invention, the term "mean diameter" is intended to mean the harmonic mean of the diameters of the particles. The nanoparticle size distribution is, for example, measured using a commercial particle sizer, such as a Malvern Zeta Sizer Nano-S particle sizer based on PCS (Photon Correlation Spectroscopy) which is characterized by a mean hydrodynamic diameter. A method of measuring this parameter is also described in standard ISO 13321:1996.

The term "polysiloxane-based nanoparticles" is intended to mean nanoparticles characterized by a weight percentage of silicon of at least 8%.

The term "polysiloxane" denotes an inorganic crosslinked polymer consisting of a series of siloxanes.

The polysiloxane structural units, which may be identical or different, have the formula below:

$$Si(OSi)_n R_{4-n}$$

in which

R is an organic molecule bonded to the silicon by an Si—C covalent bond, n is an integer between 1 and 4.

By way of preferred example, the term "polysiloxane" encompasses in particular polymers resulting from the condensation, by the sol-gel process, of tetraethylorthosilicate (TEOS) and of aminopropyltriethoxysilane (APTES).

In one specific embodiment, the nanoparticles that can be used in the preparation of the nanovectors are nanoparticles based on polysiloxane and chelates optionally complexed with metal elements.

In this preferred embodiment, they comprise or consist essentially of the following elements:
(i) polysiloxanes, with a silicon weight ratio of at least 8% of the total weight of the nanoparticle, preferably between 8% and 50% of the total weight of the nanoparticle,
(ii) chelating agents, preferably in a proportion of between 5 and 100, and preferably between 5 and 20 per nanoparticle,
(iii) where appropriate, metal elements, preferably in a proportion of between 5 and 100, for example between 5 and 20 per nanoparticle, said metal elements being complexed with the chelating agents.

For the purpose of the present disclosure, the term "chelating agent" is intended to mean an organic group capable of complexing a metal cation. For example, in one specific embodiment, the chelating agent is selected from those of which the complexation constant $\log(K_{CI})$ is greater than 15, preferentially 20 with respect to the targeted metal cation.

Thus, the function of the chelating agent is to complex the optional inorganic elements of the nanovector (metal cations for example) and to reduce the release thereof after the administration of the nanovector in human beings or animals.

The chelating agent can be obtained by grafting (covalent bonding), onto the nanoparticle, of one of the following products (before grafting on the nanoparticle):

polycarboxylic polyamino acids and derivatives thereof, and even more preferentially from the group consisting of: DOTA (1,4,7,10-tetraazacyclododecane-N,N',N",N"'-tetraacetic acid), DTPA (diethylenetriaminepentaacetic acid), DO3A-pyridine of formula (I) below:

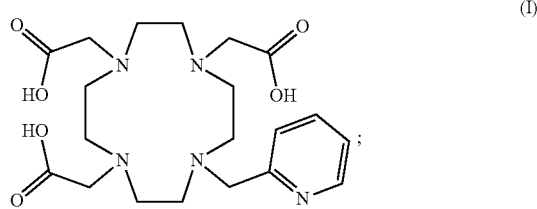 [SMILES: O=C(O)CN1CCN(CC(=O)O)CCN(Cc2ccccn2)CCN(CC(=O)O)CC1]

EDTA (2,2',2",2"'-(ethane-1,2-diyldinitrilo)tetraacetic acid), EGTA (ethylene glycol-bis(2-aminoethyl ether)-N,N,N',N'-tetraacetic acid), BAPTA (1,2-bis(o-aminophenoxy)ethane-N,N,N',N'-tetraacetic acid), NOTA (1,4,7-triazacyclononane-1,4,7-triacetic acid), PCTA (3,6,9,15-tetraazabicyclo[9.3.1.]pentadeca-1(15),11,13-triene-3,6,9-triacetic acid), DOTAGA (2-(4,7,10-tris(carboxymethyl)-1,4,7,10-tetraazacyclododecan-1-yl) pentanedioic acid), and TMPAC of formula (II) below:

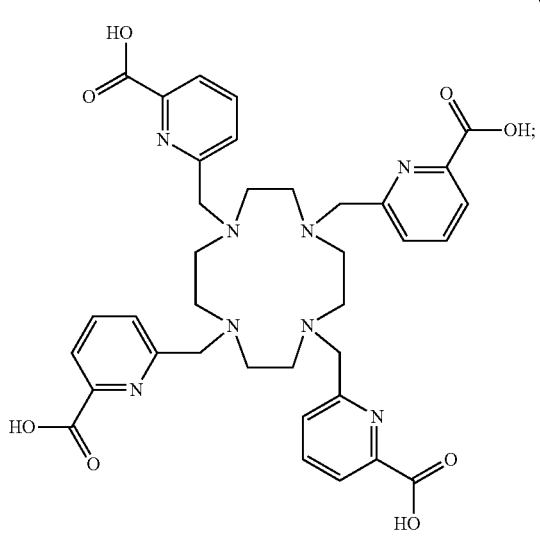

and mixtures thereof;
the products of the group comprising porphyrin, chlorine, 1,10-phenanthroline, bipyridine, terpyridine, cyclam, triazacyclononane, derivatives thereof and mixtures thereof;
and mixtures thereof.

Preferably, said chelating agents above are directly or indirectly bonded, by covalent bonding, to the silicons of the polysiloxanes of the nanoparticle. The term "indirect" bonding is intended to mean the presence of a molecular "linker" or "spacer" between the nanoparticle and the chelating agent, said linker or spacer being covalently bonded to one of the constituents of the nanoparticle.

In one preferred embodiment, the chelating agent is obtained by grafting of DOTAGA onto the nanoparticle.

In one embodiment, the nanoparticles that can be used for the preparation of the nanovectors do not comprise metal elements.

In another embodiment, the nanoparticles can comprise metal elements, in an ionic form, for example a cation, or a non-ionic form.

By way of examples of metal cations, it will be possible to preferably choose the metal cations that can be complexed by chelating agents, and in particular, according to the desired applications, alkaline-earth metal cations,
alkali metal cations and the radioactive isotopes thereof,
transition metal cations and the radioactive isotopes thereof,
post-transition metal cations and the radioactive isotopes thereof,
rare earth cations and the radioactive isotopes thereof,
and mixtures thereof.

In another embodiment, the metal elements are chosen from alkaline-earth metal cations and in particular magnesium and/or calcium.

In particular, depending on the desired applications, the metal elements are chosen from metal cations with a high atomic number Z.

In the text which follows, the term "high-Z element" will refer to an element (in its ionic or non-ionic form) with an atomic number Z of at least greater than 40, preferably greater than 50.

The metal elements with a high atomic number Z are useful in particular for combined uses of the nanovectors for delivery of anti-cancer substances and an action as a scans contrast agent or as a radiosensitizing agent in radiotherapy.

For combined use of the nanovector for delivery of anti-cancer substances and an action in curietherapy or scintigraphy, the metal elements can also be chosen from the appropriate isotopes.

For a combined use of the nanovector for delivery of anti-cancer substances and in magnetic resonance imaging, metal elements with appropriate magnetic properties may also be chosen.

The transition metals comprise in particular Hf, Cu, Pt, Au, Tc, Y, Mn, Ru, Fe and Zr, and mixtures thereof.

The post-transition metals include Bi, Ga and In, and mixtures thereof.

The rare earth metals include the lanthanides, such as Gd, Dy, Eu, Tb, Nd, Yb, Er, Ho and Lu, and mixtures thereof, and preferably Gd.

Gd, Dy, Mn and Fe are more particularly useful for use as a contrast agent in magnetic resonance imaging (MRI).

Eu, Tb, Nd, Yb and Er are more particularly useful for use as a fluorescent agent in imaging.

Ho, Bi, Y and Lu are particularly useful for use as an agent in curietherapy.

Lu, Yb, Gd, Bi, Hf and Ho are particularly useful for use as a radiosensitizing agent.

Cu, Ga, Tc, Y, In and Zr are particularly useful for use as a probe in scintigraphy.

In one particular embodiment, the ratio of high-Z element per nanoparticle (for example, a lanthanide, for example Gd), is between 5 and 100 high-Z elements per nanoparticle, preferably between 5 and 20.

In an even more preferred embodiment, the nanoparticles comprise:

polysiloxanes,

DOTAGA as chelating agent covalently bonded to the polysiloxanes, $Gd^{3+}$ cations complexed to the chelating agents.

The nanoparticles based on polysiloxane and on metal element chelates are well known to those skilled in the art. Preferred embodiments are described in particular in the following publications: WO 2011/135101, WO 2013/153197.

Ultrafine Nanoparticles

A more particularly preferred embodiment for the preparation of the nanovectors according to the present disclosure is the nanoparticles termed "ultrafine" or "inorganic-core-free", based on polysiloxane and having a mean diameter of less than 10 nm, or even less than 5 nm.

These ultrafine nanoparticles in fact accumulate the advantages of multimodality and of passive targeting of tumours (without the presence of targeting molecules at their surface), in particular by EPR ("Enhanced Permeability and Retention") effect. They are therefore particularly suitable for the preparation of the nano vectors according to the present disclosure, in particular in combination with anti-cancer substances for applications in anti-cancer therapy, and in particular in chemotherapy or combining chemotherapy and at least one other therapy chosen from radiotherapy or curietherapy.

In addition to their small size, they are characterized by the absence of an inorganic core based on a metal element, contrary to numerous nanoparticles of core-shell type. The ultrafine nanoparticles can be characterized by formula (I) below:

$$Si_n[O]_m[OH]_o[Ch_1]_a[Ch_2]_b[Ch_3]_c[M^{y+}]_d[D^{z+}]_e[Gf]_f \quad (I)$$

in which:
n is between 20 and 5000, preferentially between 20 and 200,
m is greater than n and less than 4 n,
o is between 0 and 2 n,
$Ch_1$, $Ch_2$ and $Ch_3$ are potentially chelating organic groups, which may be identical or different, linked to the Si atoms of the polysiloxanes by an Si—C covalent bond; a, b and c are integers between 0 and n and a+b+c is less than or equal to n, preferably a+b+c is between 5 and 100, for example between 5 and 20,
$M^{y+}$ and $D^{z+}$ are metal cations, which may be identical to or different from one another, with y and z=1 to 6; and d and e are integers between 0 and a+b+c, and d+e is less than or equal to a+b+c,
Gf are targeting grafts, which may be identical to or different from one another, each linked to the Si by an Si—C bond and resulting from the grafting of a targeting molecule allowing the targeting of the nanoparticles to biological tissues of interest, for example to tumour tissues, f is an integer between 0 and n.

In one particular embodiment, the ultrafine nanoparticle has the chemical formula (II) below:

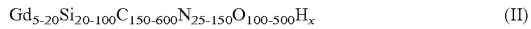

$$Gd_{5-20}Si_{20-100}C_{150-600}N_{25-150}O_{100-500}H_x \quad (II)$$

H being dependent on the number of the other atoms and difficult to measure, for example by elemental analysis, the number x (integer) is not indicated in formula (II).

These nanoparticles preferably have a mean diameter of less than 5 nm.

In the interests of convenience, the nanoparticles of formula (I) or formula (II) are hereinafter referred to as "ultrafine nanoparticles".

These nanoparticles of general formula above are advantageously obtained according to one of the modes described below.

Methods for Obtaining the Ultrafine Nanoparticles

The ultrafine nanoparticles can be obtained by means of an original "top-down" method, the essential steps of which are as follows:
a. preparing an inorganic core of metal element (M) oxide, M preferably being chosen from rare earth metals and transition elements, optionally doped with a doping agent (D), D being a metal element different from M, chosen from rare earth metals and/or transition elements,
b. synthesizing a polysiloxane shell around the core of metal element (M) oxide, by sol-gel condensation,
c. grafting a chelating agent onto the polysiloxane, by —Si—C— covalent bonding, so as to obtain a core-shell precursor nanoparticle, and
d. transferring the core-shell precursor nanoparticle into an aqueous solution, said chelating agent being in an amount sufficient to induce dissolution of the inorganic core of metal element (M) oxide and to form complexes with said metal element (M) and where appropriate the doping agent (D),
said dissolution of the inorganic core leading to a reduction in the diameter of the final nanoparticle relative to the precursor nanoparticle, for a final mean diameter of the ultrafine particle of between 1 and 5 nm.

In practice, the process will be carried out in the following way:

A precursor nanoparticle of core/shell type with a core of metal element oxide, for example of rare earth oxide, is prepared via the polyol route modified with a polysiloxane shell by sol/gel synthesis; this object has for example a size of between 5 and 10 nm.

More specifically, an inorganic core of metal element oxide of very small size (which can be adjusted, less than 10 nm) can be produced in an alcohol by one of the methods described in the following publications (P. Perriat et al., J. Coll. Int. Sci, 2004, 273, 191; O. Tillement et al., J. Am. Chem. Soc., 2007, 129, 5076 and P. Perriat et al., J. Phys. Chem. C, 2009, 113, 4038). After the step of synthesizing the inorganic core, these inorganic cores can be coated with a layer of polysiloxane by following for example a protocol described in the following publications: C. Louis et al., Chem. Mat., 2005, 17, 1673 and O. Tillement et al., J. Am. Chem. Soc., 2007, 129, 5076.

Next, chelating agents specific for the targeted metal elements are grafted at the surface of the polysiloxane; a part of said chelating agents can also be inserted inside the layer, but the control of the formation of the polysiloxane is complex and simple external grafting gives, at these very small sizes, a sufficient grafting proportion.

The nanoparticles can then be separated from the synthesis residues by means of a method of dialysis or of tangential filtration, on a membrane comprising pores of suitable size.

In a subsequent step, the inorganic core is destroyed by dissolution after transfer into aqueous medium (for example by modifying the pH or by introducing chelating agents into the solution). This destruction of the inorganic core then allows scattering of the polysiloxane layer (according to a mechanism of slow corrosion or collapse), which makes it possible to finally obtain the ultrafine nanoparticle, that is to say a polysiloxane object of complex morphology, the characteristic dimensions of which are of the order of magnitude of the thickness of the initial polysiloxane layer.

The ultrafine nanoparticle has a high content of chelating agent and of metal element since they are initially grafted at the surface of the polysiloxane and at these very small sizes, the surface involves a very high proportion of the material of the particle; the surface to volume ratio varies as a function of the size as 1/r (radius). During the mechanism of collapse of this structure, other complexes can also bind, up to saturation, to the newly formed "fresh" surfaces. Complexing agent contents are thus achieved which are much higher than those that would have been obtained with a conventional functionalization of the surface of finer silica particles, with the proviso of the availability of such particles. In particular, the chelating agent to nanoparticle ratio can be between 5 and 100 and preferentially between 5 and 20.

Removing the core thus makes it possible to decrease from a mean particle diameter of approximately 5 nanometres or more to sizes of less than 5 nm. Furthermore, this operation makes it possible to increase the number of metal elements M (e.g. gadolinium) per $nm^3$ in comparison with a theoretical polysiloxane nanoparticle of the same size but comprising M (e.g. gadolinium) only at the surface.

The number of metal elements M for a nanoparticle size can be evaluated by virtue of the M/Si atomic ratio measured by EDX or by elemental analysis. It is generally substantially similar to the number of chelating agents per nanoparticle, and is for example between 5 and 100 and preferentially between 5 and 20.

Further details regarding these ultrafine nanoparticles, the methods for synthesizing them and the applications thereof are described in patent application WO 2011/135101, which is incorporated by way of reference, and in the article by Mignot et al., 2013, *Chem. Eur. J.* 2013, 19, 6122-6136.

Nanoparticles by "One Pot" Synthesis

In another embodiment, the inorganic-core-free ultrafine nanoparticles with a diameter of less than 10 nm and comprising polysiloxanes, where appropriate metal-element-chelating agents, can be obtained by means of the following method:

The "one pot" synthesis method consists in mixing at least one silane which is negatively charged at physiological pH with at least one silane which is neutral at physiological pH, and/or at least one silane which is positively charged at physiological pH, wherein:

the molar ratio A of the number of neutral silanes to the number of negatively charged silanes is between: 0≤A≤6, preferentially 0.5≤A≤2;

the molar ratio B of the number of positively charged silanes to the number of negatively charged silanes is between: 0.25≤B≤3, preferentially 0.5≤B≤2;

the molar ratio C of the number of positively charged or neutral silanes to the number of negatively charged silanes is between: 0≤C≤8, preferentially 1≤C≤4.

Said nanoparticles can then incorporate additional molecules, such as chelating agents or targeting grafts.

The term "physiological pH" corresponds to a pH of 7.4.

The term "silane" refers to compounds comprising a silicon atom surrounded by 4 substituents.

In the preferred embodiments, the silanes are chosen from alkoxysilanes, hydroxysilanes and mixtures thereof. The following examples are examples of silanes that can be used in this embodiment: tetraethyl orthosilicate ($Si(OC_2H_5)_4$, also known as TEOS), tetramethyl orthosilicate ($Si(OCH_3)_4$, also known as TMOS), (3-aminopropyl)triethoxysilane ($H_2N(CH_2)_3$—$Si(OC_2H_5)_3$, also known as APTES), APTES-DOTAGA, N-(trimethoxysilylpropyl)ethylenediamineacetic triacid trisodium salt (($CH_3O)_3Si$—$(CH_2)_3N(CH_2COONa)(CH_2)_2N(CH_2COONa)_2$, also known as TANED), and carboxyethylsilanetriol sodium salt, (($HO)_3Si$—$(CH_2)_2COONa$, also known as CEST).

The term silane used herein also comprises silane compounds comprising a chelated metal cation. The term silane used herein also comprises compounds resulting from the covalent grafting of any targeting agent described below to a silane precursor.

The term "alkoxysilane" denotes herein compounds of formula (III):

$$R_nSi(OR_i)_{4-n} \quad (III)$$

wherein:

R is an organic group, $R_i$ is an alkyl group comprising 1 to 12 carbons, preferentially 1 to 6 carbons, n is equal to 0, 1, 2 or 3.

According to one specific embodiment, n is equal to 0 or 1.

The term "hydroxysilane" denotes herein compounds of formula (IV):

$$R_nSi(OH)_{4-n} \quad (IV)$$

wherein:

R is an organic group, n is equal to 0, 1, 2 or 3.

According to one specific embodiment, n is equal to 0 or 1.

The term "organic group" used herein refers to any organic group, regardless of the functional group involved which is bonded to the silicon atom by an Si—C bond. An example of an organic group comprises, without limitation, alkylamines.

The term "alkyl group" used herein refers to linear or crosslinked alkyl groups. The desired alkyl groups include: methyl, ethyl, n-propyl, i-propyl, n-butyl, i-butyl, s-butyl and t-butyl, pentyl and its isomers (i.e. n-pentyl and isopentyl), and also hexyl and its isomers (i.e. n-hexyl and isohexyl).

According to one preferential embodiment, the nanoparticles obtained have a mean diameter of between 0.5 and 15 nm and preferentially between 0.5 and 10 nm.

In some specific embodiments, the silanes (chosen from alkoxysilanes, hydroxysilanes and mixtures thereof), can represent at least 80%, 85% or 90% of the total weight of the reagents, the reagents being the starting chemical compounds used for the synthesis of the nanoparticles.

The reaction can be carried out in a protic solvent, such as an alcohol or an aqueous solution. In one specific embodiment, the only solvent used is water. In other embodiments, the reaction is carried out in an alcohol or else in alcohol mixtures. The alcohols that can be used for this embodiment are included in the list: ethanol, n-propanol, isopropanol, n-butanol, tert-butanol, n-pentanol, ethylene glycol and diethylene glycol.

The reaction is preferentially carried out in a colloidal solution, which allows better control of the size of the nanoparticles. Thus, the reaction is not carried out by a conventional sol-gel process in order to avoid the formation of crosslinked gels.

One of the advantages of this method is that it can possibly be carried out by means of a "one pot" reaction, making it possible to avoid the steps of purifying and isolating intermediate products.

An advantage is that the choice of specific ratios A, B and C allows a control of the surface charge and also of the size of the silica particles, especially for the production of nanoparticles with hydrodynamic diameters of between of 0.5 and 15 nm. In particular, in order to reduce the size of the nanoparticles below 10 nm, it is preferable to have a ratio which is for example below 2 and more preferentially below 1.5.

According to one specific embodiment, the mixing steps comprise at least one positively charged silane, the positively charged silane comprising at least one positively charged amine function. APTES is an example of a silane comprising a positively charged amine function.

In one embodiment, the reaction comprises the mixture of at least one hydroxysilane or alkoxysilane which is negatively charged at physiological pH and which comprises at least one chelating agent with:
- at least one hydroxysilane or alkoxysilane which is neutral at physiological pH, and/or
- at least one hydroxysilane or alkoxysilane which is positively charged at physiological pH and which comprises an amine function,
wherein:
- the molar ratio A of the number of neutral silanes to the number of negatively charged silanes is between: $0 \le A \le 6$, preferentially $0.5 \le A \le 2$;
- the molar ratio B of the number of positively charged silanes to the number of negatively charged silanes is between: $0 \le B \le 5$, preferentially $0.25 \le B \le 4$;
- the molar ratio C of the number of positively charged or neutral silanes to the number of negatively charged silanes is between: $0 \le C \le 8$, preferentially $1 \le C \le 4$.

In accordance with one specific embodiment, the synthesis comprises a mixture of at least one alkoxysilane which is negatively charged at physiological pH, said alkoxysilane being chosen from APTES-DOTAGA, TANED and CEST and mixtures thereof, with:
- at least one alkoxysilane which is neutral at physiological pH, said alkoxysilane being chosen from TMOS, TEOS and mixtures thereof, and/or
- APTES which is positively charged at physiological pH, wherein:
- the molar ratio A of the number of neutral silanes to the number of negatively charged silanes is between: $0 \le A \le 6$, preferentially $0.5 \le A \le 2$;
- the molar ratio B of the number of positively charged silanes to the number of negatively charged silanes is between: $0 \le B \le 5$, preferentially $0.25 \le B \le 4$;
- the molar ratio C of the number of positively charged or neutral silanes to the number of negatively charged silanes is between: $0 \le C \le 8$, preferentially $1 \le C \le 4$.

In accordance with one specific embodiment, the synthesis comprises the mixture of APTES-DOTAGA which is negatively charged at physiological pH and of:
- at least one alkoxysilane which is neutral at physiological pH, said alkoxysilane being chosen from TMOS, TEOS and mixtures thereof, and/or
- APTES which is positively charged at physiological pH, wherein:
- the molar ratio A of the number of neutral silanes to the number of negatively charged silanes is between: $0 \le A \le 6$, preferentially $0.5 \le A \le 2$;
- the molar ratio B of the number of positively charged silanes to the number of negatively charged silanes is between: $0 \le B \le 5$, preferentially $0.25 \le B \le 4$;
- the molar ratio C of the number of positively charged or neutral silanes to the number of negatively charged silanes is between: $0 \le C \le 8$, preferentially $1 \le C \le 4$.

The Targeting Molecules

The nanoparticles can also comprise targeting agents directly or indirectly covalently bonded to the silicons of the nanoparticles. Examples of targeting molecules are described below. The targeting agents are grafted at the surface of the nanoparticles and are present in a proportion of between 1 and 20 targeting agents per nanoparticle, and preferably between 1 and 5 targeting agents.

For the surface grafting of the targeting molecules, use may be made of a conventional coupling with reactive groups which are present, optionally preceded by an activation step. The coupling reactions are known to those skilled in the art and will be chosen according to the structure of the surface layer of the nanoparticle and to the functional groups of the targeting molecule. See, for example, "*Bioconjugate Techniques*", G. T Hermanson, Academic Press, 1996, in "*Fluorescent and Luminescent Probes for Biological Activity*", Second Edition, W. T. Mason, ed. Academic Press, 1999. Preferred coupling methods are described below. Preferably, these targeting molecules are grafted to the chelating agents of nanoparticles according to the "core-free" ultrafine nanoparticle variant as described in the preceding section.

The targeting molecules will be chosen according to the envisaged application.

In one particular embodiment, molecules suitable for the active targeting of tumours will be chosen. By way of example of targeting molecules which can be grafted onto the nanoparticles, mention may be made of molecules containing the RGD tripeptide capable of recognizing the $\alpha v \beta 3$ integrin. Such peptides and derivatives thereof (in particular cyclic pentapeptide) are described in particular in WO 2004/026894.

Targeting molecules suitable for the targeting of tumour tissues have been described for example in International publication WO 01/00621 and include quaternary ammonium derivatives, aptamers, polypeptides, antibodies, etc.

Active Substances that can be Used in the Preparation of the Nanovectors

For the purposes of the present invention, the term "active substance" is intended to mean:
(i) any substance which has curative or preventive properties with regard to human or animal diseases,
(ii) any substance which can be used in human beings or animals or which can be administered thereto with a view to restoring, correcting or modifying physiological functions by exercising a pharmacological, immunological or metabolic action.

Preferably, the active substances that can be used in the preparation of the nanovectors according to the present disclosure are organic molecules.

In the present disclosure, the term "organic molecule" is intended to mean a molecule consisting essentially of the following elements: C, H, O, N, P, S. They may be molecules of biological or synthetic origin. The term "organic molecule" also encompasses, for the purposes of the present invention, organic compounds which chelate a metal, in particular a metal chosen from Pt, Ti, Ru, Au and Rh.

In particular, the active substances that can be used in the preparation of the nanovectors are chosen from organic molecules which have a molecular weight of between 2% and 40% of the weight of the nanoparticle and preferably between 5% and 25% of the weight of the nanoparticle.

In one specific embodiment, the active substances that can be used in the preparation of the nanovectors are organic molecules which have a molecular weight of at most 5000 g·mol$^{-1}$ and preferably of between 100 and 2000 g·mol$^{-1}$ (hereinafter denoted "small molecule").

In another embodiment, they are nucleic acids, and in particular oligonucleotides, ribonucleic acids (RNAs), microRNAs, siRNAs (short interfering RNA) or iRNA (interfering RNA).

In another embodiment, they are peptides of at most 50 amino acids, for example between 5 and 30 amino acids.

In one particular embodiment, the active substance is chosen from anti-cancer substances.

By way of examples of anti-cancer substances, mention may be made of the following molecules: actinomycin, all-trans retinoic acid, azacitidine, azathioprine, bleomycin, bortezomib, carboplatin, capecitabine, cisplatin, chlorambucil, cyclophosphamide, cytarabin, daunorubicin, docetaxel, doxifluridine, doxorubicin, epirubicin, epothilone, etoposide, fluorouracil, gemcitabine, hydroxyurea, darubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vemurafenib, vinblastine, vincristine, vindesine, lenalidomide, ibrutinib, abiraterone, erlotinib, everolimus, nilotinib, sunitinib, sorafenib, goserelin, nedaplatin, laboplatin and heptaplatin, or mixtures thereof.

In one specific embodiment, the active substance is chosen from doxorubicin, the TATE peptide and cisplatin, or mixtures thereof.

Preparation of the Nanovectors According to the Present Disclosure

The method for preparing the nanovectors according to the present disclosure consists in mixing two solutions that can be administered in human beings or animals:
- a first solution comprising a polysiloxane-based nanoparticle with a mean diameter of less than 10 nm, preferably less than 5 nm, and
- a second solution comprising an active substance or a mixture of active substances,
- under concentration ratio, pH and temperature conditions which allow an interaction by physisorption of the active substances at the surface of said nanoparticles.

For the purposes of the present disclosure, the term "interaction by physisorption" is intended to mean Van der Waals interactions, excluding in particular specific protein/protein interactions of the type ligand/receptor, antigen/antibody or other molecule-specific molecule interactions, etc.

The nanoparticles and active substances that can be used for the preparation of the nanovectors and in particular certain preferred embodiments have been described in the preceding sections.

For the purposes of the present disclosure, the load content corresponds to the amount of active substances linked to the nanovector, expressed in mg per gram of nanoparticles.

In one specific embodiment, the [active substances in the second solution]: [nanoparticles in the first solution] concentration ratio by weight is determined so as to allow an active substance load content of greater than 0.5 mg/g, preferentially 1 mg/g of nanoparticles, for example between 1 mg/g and 100 mg/g.

Those skilled in the art will be able to easily determine the optimal concentration, pH and temperature ratios according to the structure of the nanoparticles and active substances chosen, in particular in order to optimize the active substance load content.

In one particular embodiment, the first solution is an aqueous colloidal solution of nanoparticles (for example ultrafine nanoparticles) at a concentration of between 5 and 500 g·L$^{-1}$, at a pH of between 6 and 8.

In one particular embodiment, which can preferentially be combined with the preceding embodiment, the second solution is an aqueous solution of active substances at a concentration of between 1 mg·L$^{-1}$ and 10 g·L$^{-1}$ at a pH of between 6 and 8.

The inventors have demonstrated that the active substances can be linked by physisorption at the surface of the polysiloxane-based nanoparticles, by simple mixing of the two solutions.

Thus, advantageously, it is not necessary to purify the nanovectors obtained after the mixing step before administering them in the subject.

However, if required, it is possible to carry out a step of purifying the nanovectors obtained after mixing of the solutions, so as to remove the possible active substances that have remained free in solution, in order to recover nanovectors comprising nanoparticles at the surface of which the active substances are bonded by physisorption.

Nanovector for the Delivery of Active Substances in Human Beings

The present disclosure thus relates to a nanovector for the delivery of active substances in human beings, comprising a nanoparticle, at the surface of which active substances are bonded by physisorption, characterized in that said nanoparticle is chosen from the polysiloxane-based nanoparticles with a mean diameter of less than 10 nm, preferably less than 5 nm, and the active substances are chosen from organic molecules which have a molar weight of between 2% and 40% of the weight of said nanoparticle, preferably between 5% and 25% of the molecular weight of said nanoparticle.

Such nanovectors can be directly or indirectly obtained by means of the simple method of mixing the 2 solutions described above.

In one particular embodiment, the nanovector comprises
(i) nanoparticles consisting essentially of the following elements:
  a. polysiloxanes, characterized by a weight percentage of silicon of between 8% and 50%,
  b. chelating agents, preferably in a proportion of between 5 and 100 per nanoparticle, and more preferentially between 5 and 20,
  c. where appropriate, metal elements, for example Gd or Bi, preferably in a proportion of between 5 and 100, and more preferentially between 5 and 20, said metal elements being complexed to the chelating agents; and
(ii) active substances bonded to the surface of the nanoparticles by physisorption.

In a more preferred embodiment of the preceding embodiment, the nanoparticles are ultrafine nanoparticles as described above. In an even more specific embodiment using ultrafine nanoparticles, the ultrafine nanoparticles comprise DOTAGA grafted to the surface of the ultrafine nanoparticles, as chelating agent, and Gd or Bi as metal element complexed to the DOTAGA.

Pharmaceutical Composition Comprising the Nanovectors

The nanovectors as described above are advantageously formulated for administration in human beings with at least one pharmaceutically acceptable excipient.

Thus, the invention relates to a pharmaceutical composition comprising nanovectors according to the present disclosure and at least one pharmaceutically acceptable excipient.

In particular, the pharmaceutical composition is an injectable pharmaceutical solution comprising a nanovector as described above, and at least one pharmaceutically acceptable excipient with an effective dose of active substances.

The pharmaceutically acceptable excipients can include any constituent which can be administered in human beings or animals and which does not substantially modify the biological activity of the active substances in the organism. They are described in particular in the reference work Remington's Pharmaceutical Sciences, Mack Publishing Company.

In one particular embodiment, said injectable pharmaceutical solution is characterized in that the nanovector comprises a metal element, preferably bismuth or gadolinium, and in that said metal element is at a concentration of between 5 and 200 mM.

In one embodiment, which can be combined with the preceding embodiment, the injectable pharmaceutical solution is characterized in that the nanovector comprises an anti-cancer active substance.

In one specific embodiment, which can be combined with the preceding embodiment(s), said active substance of the nanovector is chosen from doxorubicin, cisplatin and the TATE peptide.

Advantageously, the injectable pharmaceutical solutions are directly obtained by the step of mixing the two solutions for the preparation of the nanovectors as described above, without a subsequent purification step. They can be prepared in advance, then stored before administration to the patient, or prepared just before administration thereof to the mixture (for example less than 4 hours, less than 3 hours, less than one hour, or less than 30 minutes, or else less than 15 minutes before administration thereof to the patient), by mixing the 2 solutions.

Thus, the invention relates to a kit for preparing the nanovectors or injectable solutions as described above, the kit comprising at least two separate containers, one comprising the first solution with the nanoparticles, in a ready-to-mix form, or a concentrated form, and the other container comprising a second solution containing the active substance(s). Where appropriate, one or both of the solutions can be replaced with lyophilisates, ready to be diluted in a diluting solution so as to obtain the aqueous solutions suitable for mixing. Said diluting solution(s) optionally included in the kit can also comprise buffers or other pharmaceutically acceptable excipients with a view to administration in human beings.

Uses of the Nanovectors and Injectable Solutions According to the Present Disclosure Because of the passive-targeting properties of the nanoparticles, in particular to tumours, the nanovectors and injectable solutions described above are useful in particular for the treatment of cancer in human beings or animals, said active substance being chosen from anti-cancer substances, and in particular cytotoxic substances.

The passive targeting of tumours by polysiloxane-based nanoparticles, in particular ultrafine nanoparticles, has been described in Detappe et al., *Nano Letters* 2017; C. Verry et al., *Nanomedicine*, 2016; Dufort et al., *Small* 2015 Bianchi et al., *PNAS*, 2014.

Thus, the present disclosure also targets a method for treating cancer in a patient, comprising the administration, to said patient, of said nanovectors comprising an effective dose of anti-cancer substances as active substance for the treatment of said cancer.

Examples of anti-cancer substances have been provided in the preceding sections.

The nanovectors according to the present disclosure are useful in particular in the treatment by chemotherapy of solid tumours and in particular: central nervous system, lung, prostate, uterus, colon, pancreas, liver, kidney, breast, head and neck, or else colon tumours. This list is of course not limiting.

The nanovectors, in addition to their high active substance load content, can also comprise a high load content of radiosensitizing agent, in the form of a chelate of metal cations. Thus, in one specific embodiment, the nanovector for use thereof in the treatment of cancer is characterized in that it comprises nanoparticles comprising chelates of an element with an atomic number greater than 40, having a radiosensitizing effect, preferably ultrafine nanoparticles as described above, and in that the administration of an effective dose of said nanovector in the subject to be treated allows treatment of the cancer by combined chemotherapy and radiotherapy effect.

Advantageously, because of the physisorption of the active substances on the nanoparticles, the active substances should exhibit improved pharmacokinetics and in particular better targeting of the tumour by EPR effect as noted for the ultrafine polysiloxane nanoparticles on numerous preclinical models and described in Detappe et al., *Nano Letters* 2017; C. Verry et al., *Nanomedicine,* 2016; Dufort et al., *Small* 2015; Bianchi et al., *PNAS,* 2014.

The nanovector (or injectable solution) according to the present disclosure can be administered preferably intravenously, intratumorally, intraperitoneally, intraarterially or via the airways (for example intranasally or intratracheally), in particular as described in publication WO 2013/153197.

The nanovector can also allow treatment by radiotherapy by choosing nanoparticles comprising metal element chelates, for use as contrast agent, in particular in MRI, scans or scintigraphy.

Thus, in one particular embodiment, in which the nanovector comprises nanoparticles comprising contrast agents for imaging by magnetic resonance imaging, scans or scintigraphy, and the administration of an effective dose of said nanovector in the subject to be treated, makes it possible to monitor the curative action of the treatment.

The present disclosure also relates to a method for monitoring the therapeutic efficacy of a therapeutic treatment in human beings or animals, said method comprising the following steps:
  (i) upon initiation of the treatment, nanovectors as defined above, and comprising an effective dose of contrast agent and an effective dose of active substances, are administered to the patient,
  (ii) the images are captured by an appropriate imaging technique in order to visualize the lesions by means of the contrast agent,
  (iii) steps (i) and (ii) are repeated during the treatment of the patient, as many times as necessary,
  (iv) the therapeutic efficacy of the treatment is deduced by comparing the progression of the lesions during the treatment.

A particular application of this method relates to the monitoring of the therapeutic efficacy of a treatment in human beings or animals, for example of an anti-tumour treatment, for example by chemotherapy, radiotherapy, curietherapy, phototherapy or thermotherapy, against solid tumours.

In one preferred embodiment, the invention targets a method for monitoring the therapeutic efficacy of an anti-tumour treatment in human beings or animals, in particular a chemotherapy treatment, and where appropriate combined with a radiotherapy, curietherapy, phototherapy or thermotherapy treatment, directed against the solid tumours, said method comprising the following steps:
  (i) upon initiation of the treatment, nanovectors, as defined in the preceding sections, preferably based on ultrafine nanoparticles, comprising an effective dose of contrast agent and of anti-cancer substances, are administered to the patient suffering from a cancer with solid tumours,
  (ii) the images are captured by an appropriate imaging technique in order to detect the tumours,
  (iii) where appropriate, steps (i) and (ii) are repeated during the treatment of the patient,
  (iv) the therapeutic efficacy of the anti-cancer substances is monitored by comparing the images of the tumours obtained during the treatment.

Thus, it is possible to monitor the evolution of the tumours, in particular of the size of the tumours over time, the number of said tumours and the distribution thereof, before, during and after the treatment of the patient.

Advantageously, in the methods described above, the nanovectors can simultaneously comprise an effective dose of substances active on the tumours and, where appropriate, an effective dose of radiosensitizing, photosensitizing or radioactive agent for the treatment of the tumours and/or an effective dose of contrast agent.

Thus, in the method described above, in one particular embodiment, the nanoparticles used as contrast agent are the same as those used as radiosensitizing agent.

Other uses and embodiments are also illustrated in the examples which follow.

EXAMPLES

The examples below make it possible to illustrate the invention but are in no way limiting in nature.

Figure 1:
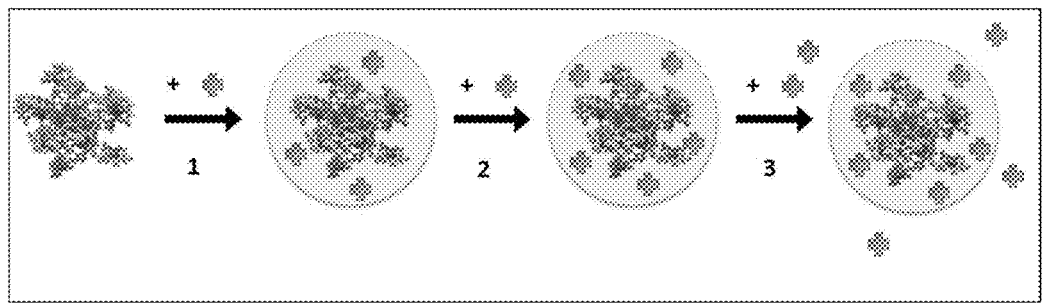
FIG. 1: General principle of the physisorption on the nanovectors. The active substance is added to the nanoparticles. Step 1: the active substance interacts by physisorption at the surface of the nanoparticles. Step 2: the active substance saturates the sphere of interaction of the nanoparticles. Step 3: the active substance can no longer interact with the surface of the nanoparticles and remains free in solution.

The aim of the various examples presented below is to illustrate the possibility of the polysiloxane nanoparticles acting as transporter of molecules used in chemotherapy. The intended molecules adsorb at the surface of the nanoparticles according to the mechanism proposed in FIG. 1. The examples below also make it possible to determine the drug concentration limit above which the drugs are no longer retained at the surface of the nanoparticle.

Figure 2:
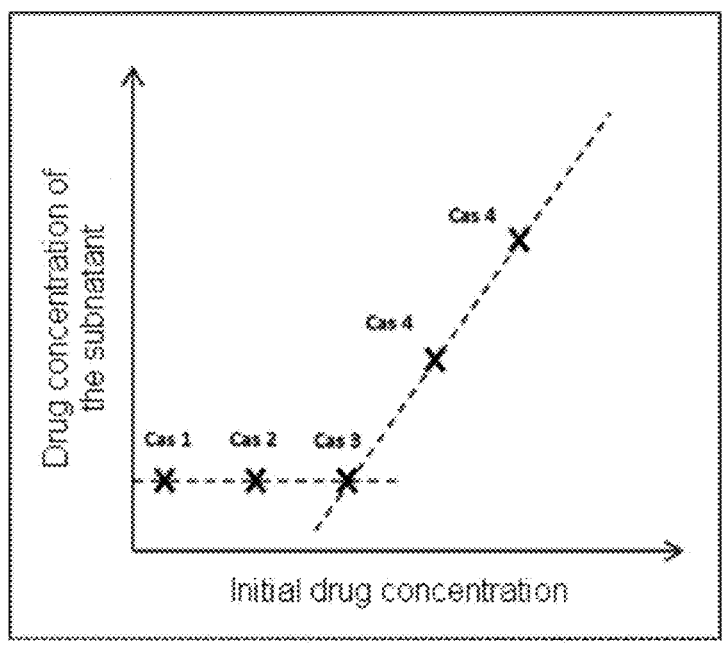
FIG. 2: Curve representing the change in concentration of active species of the subnatant as a function of the concentration of drug placed in the presence of the polysiloxane-based nanoparticles.

During the various examples, the maximum drug load content on polysiloxane nanoparticles was determined, when said particles are present at a concentration corresponding to a concentration used during clinical trials for the nanoparticle in question. Increasing concentrations of active substances were thus brought into contact with the nanoparticles. Solutions are purified by tangential filtration. The molecules which have not be able to adsorb to the surface of the nanoparticles pass through the membrane and are found in the subnatant, where they can be detected by spectroscopic techniques such as UV/Visible absorption or else fluorescence spectroscopy (FIG. 2).

Preparation of a Solution of Polysiloxane-Based Ultrafine Nanoparticles

The solution of polysiloxane-based ultrafine nanoparticles (AGuIX®) was synthesized according to the procedure described in the publication G. Le Duc et al., *Cancer Nanotechnology*, 2014.

A solution of AGuIX® at a gadolinium concentration of 10 mM is analysed by DLS with a laser at 633 nm. A number-average hydrodynamic diameter of 3.2 nm is obtained.

Nanovectors for Doxorubicin Delivery

Example 1

50 µmol ($Gd^{3+}$) of AGuIX® nanoparticles were redispersed in 125 µl of ultrapure water in order to obtain a solution at 400 mM ([$Gd^{3+}$]). 2.85 mg of doxorubicin are placed in a 2.5 ml flask. 1.1 ml of ultrapure water are added to the flask, which is stirred until the doxorubicin has completely dissolved. A solution at 2.6 g/l of doxorubicin is then obtained, and is protected from the light with aluminium. 215 µl of this solution are then added to the solution of AGuIX®, as are 160 µl of ultrapure water. The flask is stirred for 30 minutes in the dark. A solution containing 100 mM of gadolinium and 112 mg/l of doxorubicin is thus obtained.

This solution is placed in a 3 kDa Vivaspin®, and a tangential filtration cycle is carried out in order to obtain a supernatant of 200 µl. The subnatant is analysed by UV-visible analysis. The supernatant is diluted 50-fold and is analysed by UV-visible analysis.

Example 2 (Comparative)

A solution of doxorubicin at 112 mg/l is prepared according to the procedure described in Example 1, the solution of AGuIX® being replaced with ultrapure water.

Example 3

50 µmol ($Gd^{3+}$) of AGuIX® nanoparticles were redispersed in 125 µl of ultrapure water in order to obtain a solution at 400 mM ([$Gd^{3+}$]). 2.85 mg of doxorubicin are placed in a 2.5 ml flask. 1.1 ml of ultrapure water are added to the flask, which is stirred until the doxorubicin has completely dissolved. A solution at 2.6 g/l of doxorubicin is then obtained, and is protected from the light with aluminium. 327 µl of this solution are then added to the solution of AGuIX®, as are 48 µl of ultrapure water. The flask is stirred for 30 minutes in the dark. A solution containing 100 mM of gadolinium and 170 mg/l of doxorubicin is thus obtained.

This solution is placed in a 3 kDa Vivaspin®, and a tangential filtration cycle is carried out in order to obtain a supernatant of 200 µl. The subnatant is analysed by UV-visible analysis. The supernatant is diluted 50-fold and is analysed by UV-visible analysis.

Example 4 (Comparative)

A solution of doxorubicin at 170 mg/l is prepared according to the procedure described in Example 3, the solution of AGuIX® being replaced with ultrapure water.

Comparative Results Examples 1/2 and 3/4

Figure 3:
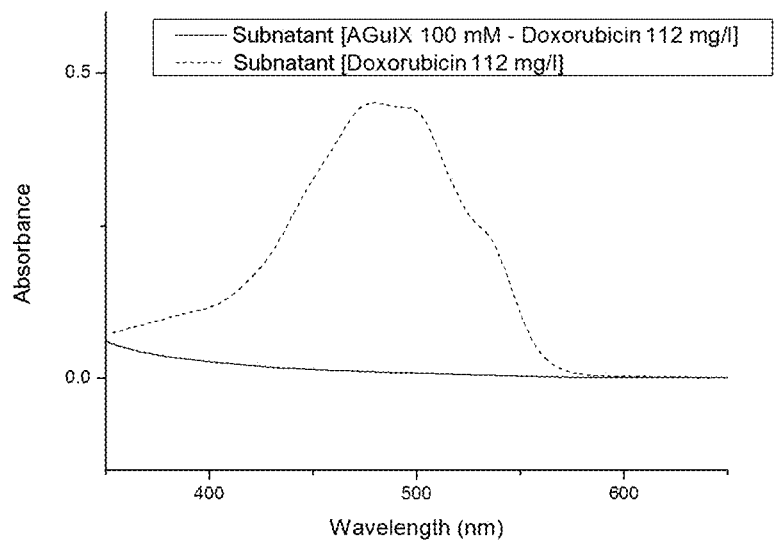
FIG. 3: Absorption spectra of the subnatants of Examples 1 and 2.
Figure 4:
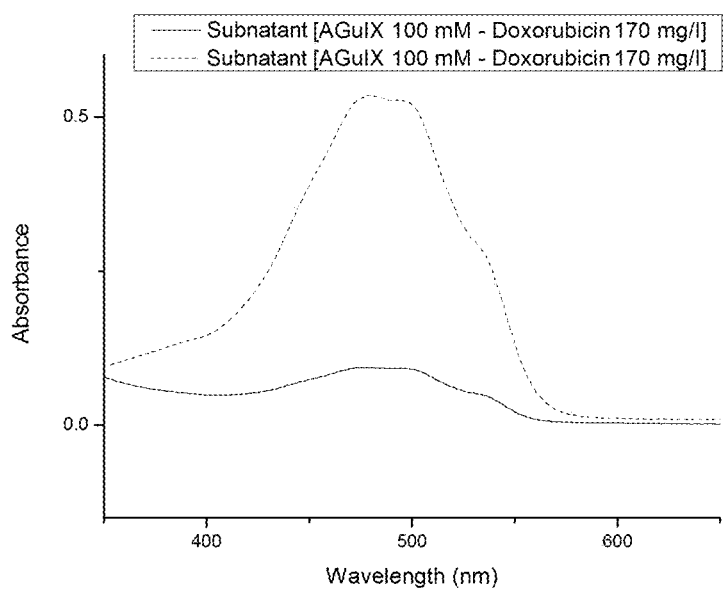
FIG. 4: Absorption spectra of the subnatants of Examples 3 and 4.

FIGS. 3 and 4 represent, respectively, the absorption spectra of the subnatants of the solutions of Examples 1 and 2, and of the solutions of Examples 3 and 4. These data show that the doxorubicin interacts with the AGuIX® nanoparticles. Indeed, for the solution containing 100 mM ([$Gd^{3+}$]) of AGuIX® and 112 mg/l, the doxorubicin is adsorbed at the surface of the nanoparticle and is not detected in the subnatant after tangential filtration, contrary to a solution of doxorubicin alone. For the solution containing 100 mM ([$Gd^{3+}$]) of AGuIX® and 170 mg/l, a very weak signal is detected by UV/VIS spectrophotometry, indicating that the majority of the doxorubicin is adsorbed at the surface of the nanoparticles and that a small amount passes through the membrane.

A solution obtained by the procedure of Example 3 (doxorubicin at 170 mg/l and AGuIX® at 100 mM [$Gd^{3+}$]) is diluted 50-fold and analysed by DLS with a laser at 633 nm. A number-average hydrodynamic diameter of 3.7 nm is obtained, which is greater than the diameter of 3.2 nm obtained for the AGuIX® nanoparticles, indicating a surface interaction of the nanoparticles with the doxorubicin.

Figure 5:
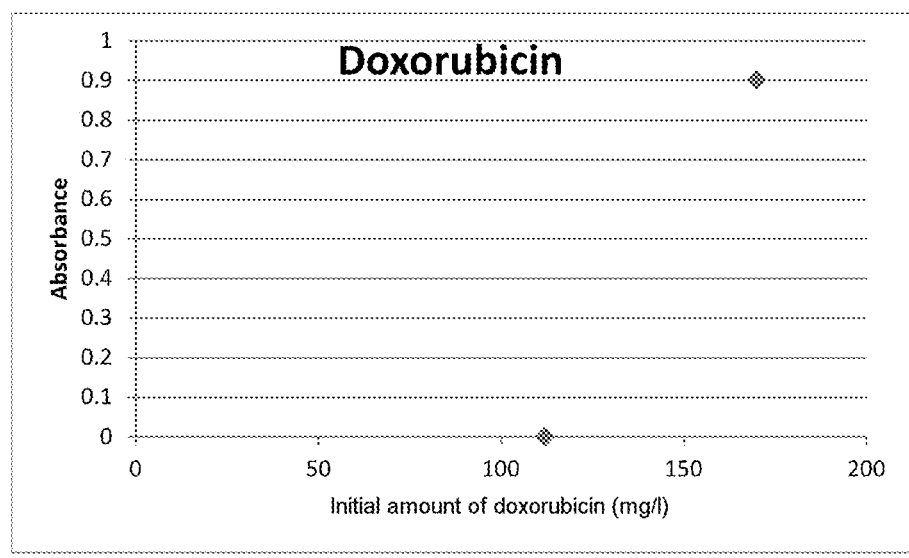
FIG. 5: Absorption values at 497 nm of the subnatants of the solutions of doxorubicin in the presence of AGuIX at 100 mM, as a function of the amount of doxorubicin introduced.

For a solution of AGuIX® nanoparticles at 100 mM ([$Gd^{3+}$]) corresponding to 100 g/l of nanoparticles, a retention of doxorubicin is observed up to a minimum concentration of 112 mg/l, which corresponds to a load content by weight greater than 1.12 mg/g of nanoparticles (FIG. 5).

Nanovectors for Delivery of TATE Peptide

Example 6

50 µmol ($Gd^{3+}$) of AGuIX® were dispersed in 125 µl of ultrapure water in order to obtain a solution at 400 mM ([$Gd^{3+}$]). 14.94 mg of tyr3-octreotate (TATE) peptide are placed in a 2.5 ml flask. 498 µl of ultrapure water are added to the flask, which is stirred until the peptide has completely dissolved. A solution containing 30 g/l of peptide is then obtained. 48 µl of this solution are then added to the solution of AGuIX®, as are 328 µl of ultrapure water. The flask is stirred for 30 minutes. A solution containing 100 mM of gadolinium and 2.90 g/l of peptide is thus obtained.

This solution is placed in a 3 kDa Vivaspin®, and a tangential filtration cycle is carried out so as to obtain a supernatant of 200 µl. The subnatant is analysed by UV-visible analysis and fluorometry after 20-fold dilution.

Example 7 (Comparative)

A solution of TATE peptide at 2.90 g/l is prepared according to the procedure described in Example 6, the solution of AGuIX® being replaced with ultrapure water.

Example 8

50 µmol ($Gd^{3+}$) of the AGuIX® nanoparticles were redispersed in 125 µl of ultrapure water in order to obtain a solution at 400 mM ([$Gd^{3+}$]). 6.1 mg of tyr3-octreotate (TATE) peptide are placed in a 2.5 ml flask. 203.3 µl of ultrapure water are added to the flask, which is stirred until the peptide has completely dissolved. A solution containing 30 g/l of peptide is then obtained. 97 µl of this solution are then added to the solution of AGuIX®, as are 279 µl of ultrapure water. The flask is stirred for 30 minutes. A solution containing 100 mM of gadolinium and 5.80 g/l of peptide is thus obtained.

This solution is placed in a 3 kDa Vivaspin®, and a tangential filtration cycle is carried out so as to obtain a supernatant of 320 µl. The subnatant is analysed by UV-visible analysis (20-fold dilution) and fluorometry (40-fold dilution).

Example 9

50 µmol ($Gd^{3+}$) of the AGuIX® nanoparticles were redispersed in 125 µl of ultrapure water in order to obtain a solution at 400 mM ([$Gd^{3+}$]). 14.94 mg of tyr3-octreotate (TATE) peptide are placed in a 2.5 ml flask. 498 µl of ultrapure water are added to the flask, which is stirred until the peptide has completely dissolved. A solution containing 30 g/l of peptide is then obtained. 193 μl of this solution are then added to the solution of AGuIX®, as are 182 μl of ultrapure water. The flask is stirred for 30 minutes. A solution containing 100 mM of gadolinium and 11.60 g/l of peptide is thus obtained.

This solution is placed in a 3 kDa Vivaspin®, and a tangential filtration cycle is carried out so as to obtain a supernatant of 200 μl. The subnatant is analysed by UV-visible analysis and fluorometry after 20-fold dilution.

Example 10 (Comparative)

A solution of TATE peptide at 11.60 g/l is prepared according to the procedure described in Example 5, the solution of AGuIX® being replaced with ultrapure water.

Example 11

50 μmol ($Gd^{3+}$) of the AGuIX® nanoparticles were redispersed in 250 μl of ultrapure water in order to obtain a solution at 200 mM ([$Gd^{3+}$]). 0.6 mg of tyr3-octreotate (TATE) peptide are placed in a 2.5 ml flask. 20 μl of ultrapure water are added to the flask, which is stirred until the peptide has completely dissolved. A solution containing 30 g/l of peptide is then obtained. 20 μl of this solution are then added to the solution of AGuIX®, as are 230 μl of ultrapure water. The flask is stirred for 30 minutes. A solution containing 100 mM of gadolinium and 1.20 g/l of peptide is thus obtained.

This solution is placed in a 3 kDa Vivaspin®, and a tangential filtration cycle is carried out so as to obtain a supernatant of 320 μl. The subnatant is analysed by UV-visible analysis (20-fold dilution) or fluorometry (40-fold dilution).

Results of Examples 6 to 10

Figure 6:
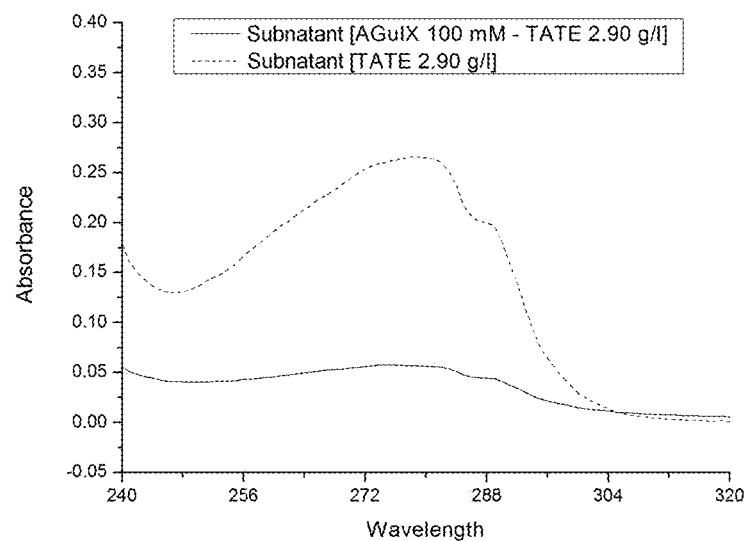
FIG. 6: Absorption spectra of the subnatants of Examples 6 and 7, diluted 20-fold.
Figure 7:
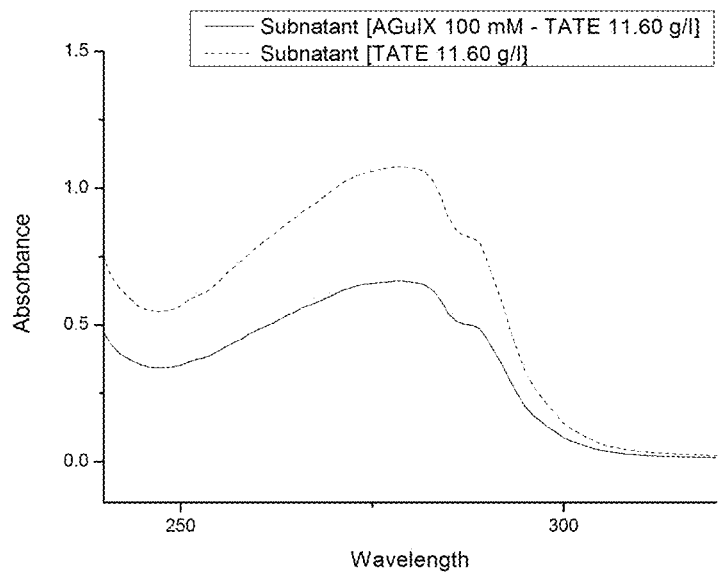
FIG. 7: Absorption spectra of the subnatants of Examples 9 and 10, diluted 20-fold.
Figure 8:
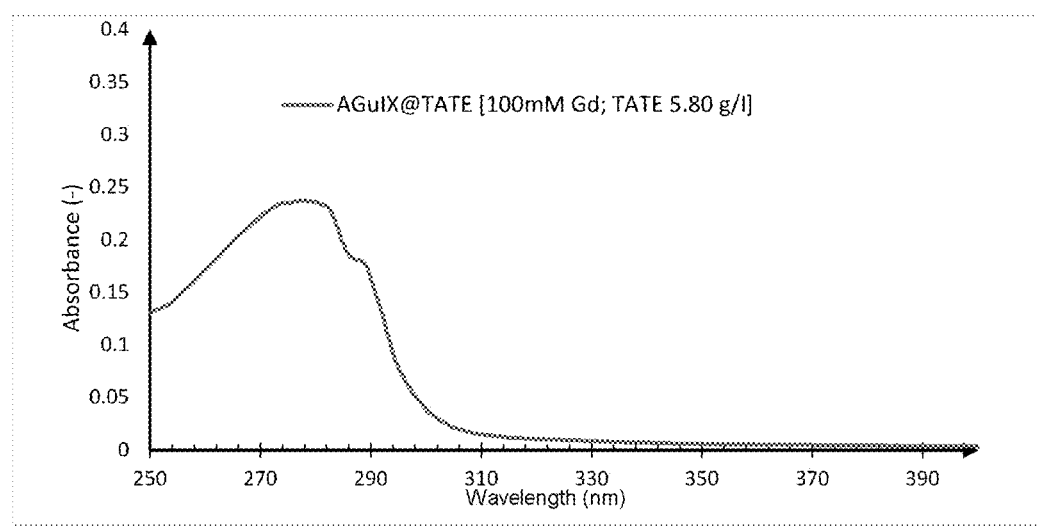
FIG. 8: Absorption spectrum of the subnatant of Example 8, diluted 20-fold.
Figure 12:
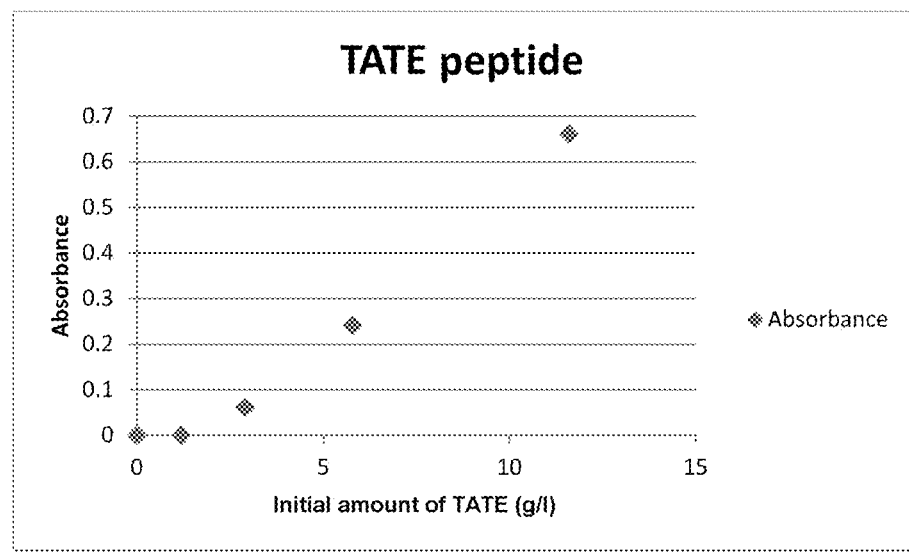
FIG. 12: Absorption values at 280 nm of the subnatants of the solutions of TATE peptide (diluted 20-fold) in the presence of AGuIX at 100 mM, as a function of the amount of TATE peptide introduced.

FIGS. 6, 7 and 8 represent, respectively, the absorption spectra of the 20-fold diluted subnatants of the solutions of Examples 6 and 7, of the solutions of Examples 9 and 10 and of the solution of Example 8. These data show that the TATE peptide adsorbs at the surface of the nanoparticles up to a concentration of approximately 2 $g \cdot L^1$ (FIG. 12). Indeed, before this limiting concentration, the TATE peptide is not detected by UV/VIS spectrophotometry in the subnatants of the solutions purified by tangential filtration.

Figure 9:
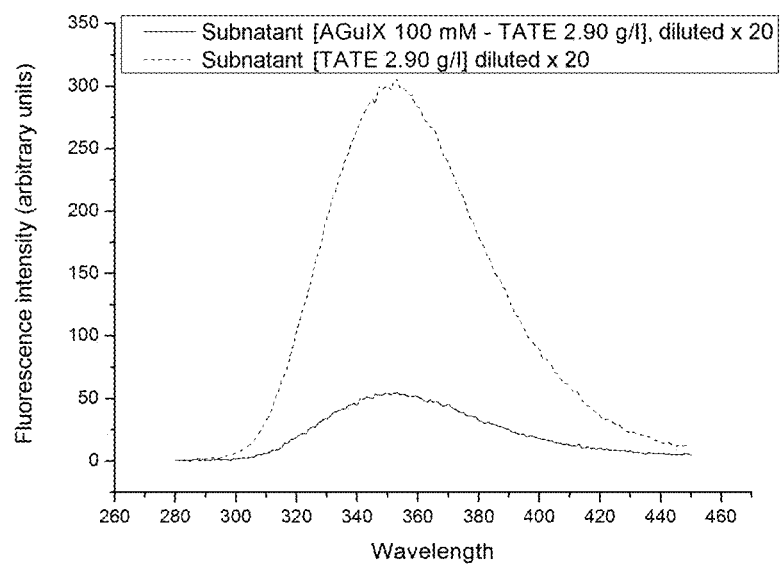
FIG. 9: Fluorescence spectrum of the subnatants of Examples 6 and 7, diluted 20-fold.
Figure 10:
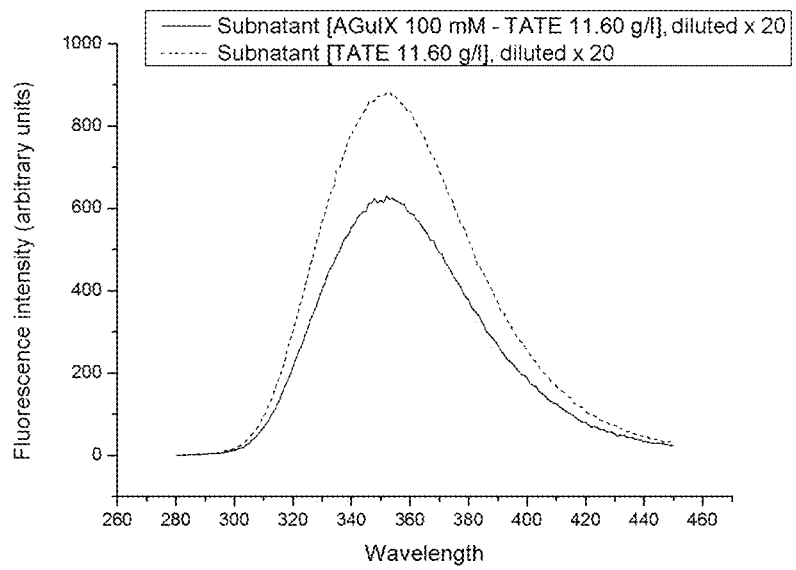
FIG. 10: Fluorescence spectrum of the subnatants of Examples 9 and 10, diluted 20-fold.
Figure 11:
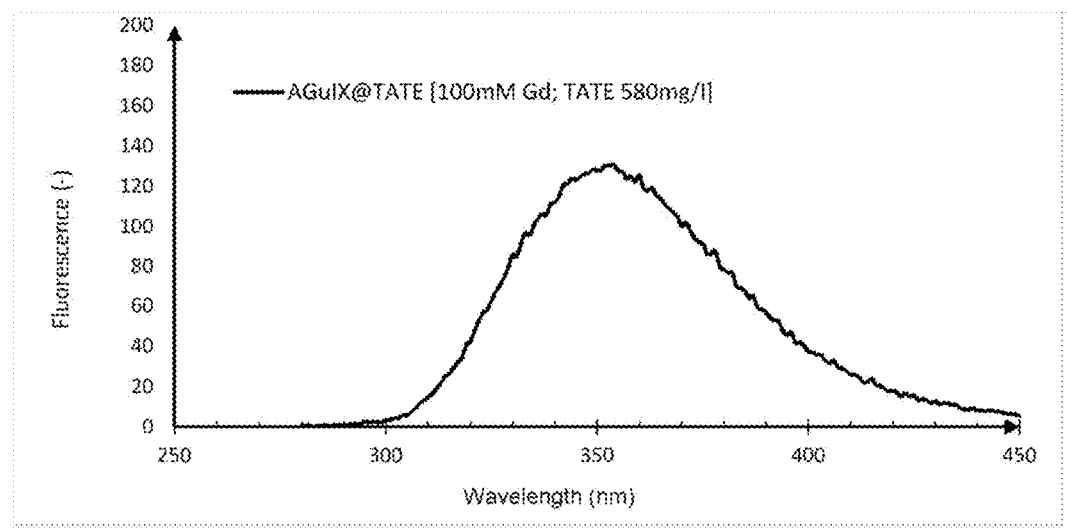
FIG. 11: Fluorescence spectrum of the subnatants of Example 8, diluted 20-fold.

FIGS. 9, 10 and 11 represent, respectively, the fluorescence spectra of the 20-fold diluted subnatants of Examples 6 and 7, of the Examples 9 and 10 and of Example 8. In the same way as for the detection by UV/VIS spectrophotometry, these data show that the TATE peptide interacts with the AGuIX® nanoparticles.

A solution obtained by the procedure of Example 8 (TATE at 2.90 g/l) is diluted 10-fold and analysed by DLS with a laser at 633 nm.

A number-average hydrodynamic diameter of 3.4 nm is obtained, which is greater than the diameter of 3.2 nm obtained for the AGuIX® nanoparticles, indicating a surface interaction of the nanoparticles with the TATE peptide.

For a solution of AGuIX® nanoparticles at 100 mM ([$Gd^{3+}$]) corresponding to 100 g/l of nanoparticles, a retention of the TATE peptide is observed up to a minimum concentration of 2 g/l, which corresponds to a load content by weight of greater than 20 mg/g of nanoparticles (FIG. 12).

Nanovectors for Delivery of Cisplatin

Example 12

50 μmol ($Gd^{3+}$) of AGuIX® were redispersed in 125 μl of ultrapure water in order to obtain a solution at 400 mM [$Gd^{3+}$]. 3.1 mg of cisplatin are placed in a 2.5 ml flask. 1.2 ml of ultrapure water are added to the flask, which is stirred. Since cisplatin is not very soluble at ambient temperature, it is necessary to heat to 40° C. until it is completely dissolved. A solution containing 2.5 g/l of cisplatin is then obtained, and is protected from the light with aluminium. 24 μl of this solution are then added to the solution of AGuIX®, as are 351 μl of ultrapure water. The flask is stirred for 30 minutes in the dark. A solution containing 100 mM of gadolinium and 120 mg/l of cisplatin is thus obtained.

This solution is placed in a 3 kDa Vivaspin®, and a tangential filtration cycle is carried out so as to obtain a supernatant of 160 μl. The subnatant is analysed by UV-visible analysis. The cisplatin is detectable by UV/VIS absorption at a wavelength of 706 nm after reaction with ODPA. For the reaction with cisplatin, a solution of ODPA at 1.4 mg/ml and a phosphate buffer (pH 6.8) are prepared. The subnatant is diluted 5-fold. 140 μl of this solution are added to 200 μl of buffer and 100 μl of ODPA. The resulting solution is heated at 100° C. for 15 min. Once the reaction is finished and the temperature has returned to ambient temperature, 560 μl of DMF are added. The final solution is filtered and then analysed by UV-visible analysis.

Example 13

50 μmol ($Gd^{3+}$) of AGuIX® were redispersed in 125 μl of ultrapure water in order to obtain a solution at 400 mM [$Gd^{3+}$]. 3.1 mg of cisplatin are placed in a 2.5 ml flask. 1.2 ml of ultrapure water are added to the flask, which is stirred. Since cisplatin is not very soluble at ambient temperature, it is necessary to heat to 40° C. until it is completely dissolved. A solution containing 2.5 g/l of cisplatin is then obtained, and is protected from the light with aluminium. 36 μl of this solution are then added to the solution of AGuIX®, as are 339 μl of ultrapure water. The flask is stirred for 30 minutes in the dark. A solution containing 100 mM of gadolinium and 180 mg/l of cisplatin is thus obtained.

This solution is placed in a 3 kDa Vivaspin®, and a tangential filtration cycle is carried out so as to obtain a supernatant of 160 μl. The subnatant is analysed by UV-visible analysis. The cisplatin is detectable by UV/VIS absorption at a wavelength of 706 nm after reaction with ODPA. For the reaction with cisplatin, a solution of ODPA at 1.4 mg/ml and a phosphate buffer (pH 6.8) are prepared. The subnatant is diluted 5-fold. 140 μl of this solution are added to 200 μl of buffer and 100 μl of ODPA. The resulting solution is heated at 100° C. for 15 min. Once the reaction is finished and the temperature has returned to ambient temperature, 560 μl of DMF are added. The final solution is filtered and then analysed by UV/VIS spectrophotometry.

Example 14

50 μmol ($Gd^{3+}$) of AGuIX® were redispersed in 125 μl of ultrapure water in order to obtain a solution at 400 mM [$Gd^{3+}$]. 3.1 mg of cisplatin are placed in a 2.5 ml flask. 1.2 ml of ultrapure water are added to the flask, which is stirred. Since cisplatin is not very soluble at ambient temperature, it is necessary to heat to 40° C. until it is completely dissolved. A solution containing 2.5 g/l of cisplatin is then obtained, and is protected from the light with aluminium. 72 µl of this solution are then added to the solution of AGuIX®, as are 303 µl of ultrapure water. The flask is stirred for 30 minutes in the dark. A solution containing 100 mM of gadolinium and 360 mg/l of cisplatin is thus obtained.

This solution is placed in a 3 kDa Vivaspin®, and a tangential filtration cycle is carried out so as to obtain a supernatant of 160 µl. The subnatant is analysed by UV-visible analysis. The cisplatin is detectable by UV/VIS absorption at a wavelength of 706 nm after reaction with ODPA. For the reaction with cisplatin, a solution of ODPA at 1.4 mg/ml and a phosphate buffer (pH 6.8) are prepared. The subnatant is diluted 5-fold. 140 µl of this solution are added to 200 µl of buffer and 100 µl of ODPA. The resulting solution is heated at 100° C. for 15 min. Once the reaction is finished and the temperature has returned to ambient temperature, 560 µl of DMF are added. The final solution is filtered and then analysed by UV-visible analysis.

Example 15

50 µmol ($Gd^{3+}$) of AGuIX® were redispersed in 125 µl of ultrapure water in order to obtain a solution at 400 mM [$Gd^{3+}$]. 2.8 mg of cisplatin are placed in a 2.5 ml flask. 1.1 ml of ultrapure water are added to the flask, which is stirred. Since cisplatin is not very soluble at ambient temperature, it is necessary to heat to 40° C. until it is completely dissolved. A solution containing 2.5 g/l of cisplatin is then obtained, and is protected from the light with aluminium. 142 µl of this solution are then added to the solution of AGuIX®, as are 233 µl of ultrapure water. The flask is stirred for 30 minutes in the dark. A solution containing 100 mM of gadolinium and 720 mg/l of cisplatin is thus obtained.

This solution is placed in a 3 kDa Vivaspin®, and a tangential filtration cycle is carried out so as to obtain a supernatant of 140 µl. The subnatant is analysed by UV-visible analysis. The cisplatin is detectable by UV/VIS absorption at a wavelength of 706 nm after reaction with ODPA. For the reaction with cisplatin, a solution of ODPA at 1.4 mg/ml and a phosphate buffer (pH 6.8) are prepared. The subnatant is diluted 5-fold. 140 µl of this solution are added to 200 µl of buffer and 100 µl of ODPA. The resulting solution is heated at 100° C. for 15 min. Once the reaction is finished and the temperature has returned to ambient temperature, 560 µl of DMF are added. The final solution is filtered and then analysed by UV-visible analysis.

Example 16 (Comparative)

A solution of cisplatin at 720 mg/l is prepared according to the procedure described in Example 15, the solution of AGuIX® being replaced with ultrapure water.

Example 17

50 µmol ($Gd^{3+}$) of AGuIX® were redispersed in 125 µl of ultrapure water in order to obtain a solution at 400 mM [$Gd^{3+}$]. 2.8 mg of cisplatin are placed in a 2.5 ml flask. 1.1 ml of ultrapure water are added to the flask, which is stirred. Since cisplatin is not very soluble at ambient temperature, it is necessary to heat to 40° C. until it is completely dissolved. A solution containing 2.5 g/l of cisplatin is then obtained, and is protected from the light with aluminium. 229 µl of this solution are then added to the solution of AGuIX®, as are 146 µl of ultrapure water. The flask is stirred for 30 minutes in the dark. A solution containing 100 mM of gadolinium and 1160 mg/l of cisplatin is thus obtained.

This solution is placed in a 3 kDa Vivaspin®, and a tangential filtration cycle is carried out so as to obtain a supernatant of 160 µl. The subnatant is analysed by UV-visible analysis. The cisplatin is detectable by UV/VIS absorption at a wavelength of 706 nm after reaction with ODPA. For the reaction with cisplatin, a solution of ODPA at 1.4 mg/ml and a phosphate buffer (pH 6.8) are prepared. The subnatant is diluted 5-fold. 140 µl of this solution are added to 200 µl of buffer and 100 µl of ODPA. The resulting solution is heated at 100° C. for 15 min.

Once the reaction is finished and the temperature has returned to ambient temperature, 560 µl of DMF are added. The final solution is filtered and then analysed by UV-visible analysis.

Results (Examples 12, 13, 14, 15 and 17)

Examples 12, 13, 14, 15 and 17 (cisplatin at 120-180-360-720-1160 mg/l) are analysed by DLS (samples diluted 10-fold) with a laser at 633 nm. The respective number-average hydrodynamic diameters are: 3.8, 3.7, 3.8, 3.4, 3.7 nm. They are greater than the diameter of 3.2 nm obtained for the AGuIX® nanoparticles, indicating a surface interaction of the nanoparticles with the cisplatin.

Example 18 (Comparative)

A solution of cisplatin at 1160 mg/l is prepared according to the procedure described in Example 15, the solution of AGuIX® being replaced with ultrapure water.

Results of Examples 15/16 and 17/18

Figure 13:
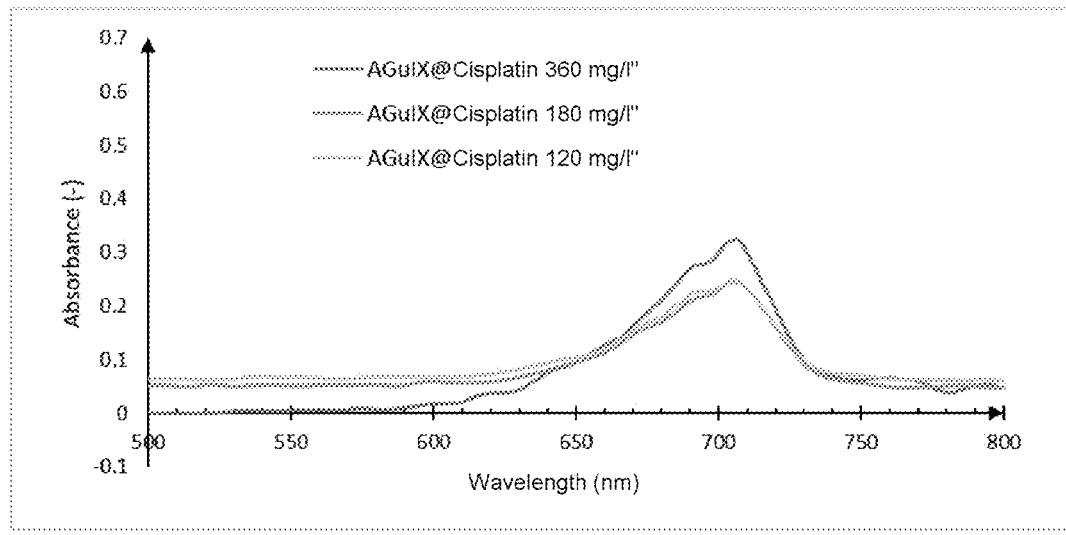
FIG. 13: Absorption spectrum of the subnatants of Examples 12, 13 and 14 after treatment as described in the examples.

FIG. 13 represents the absorbance of the subnatants of Examples 12, 13 and 14 after treatments as described in the examples.

Figure 14:
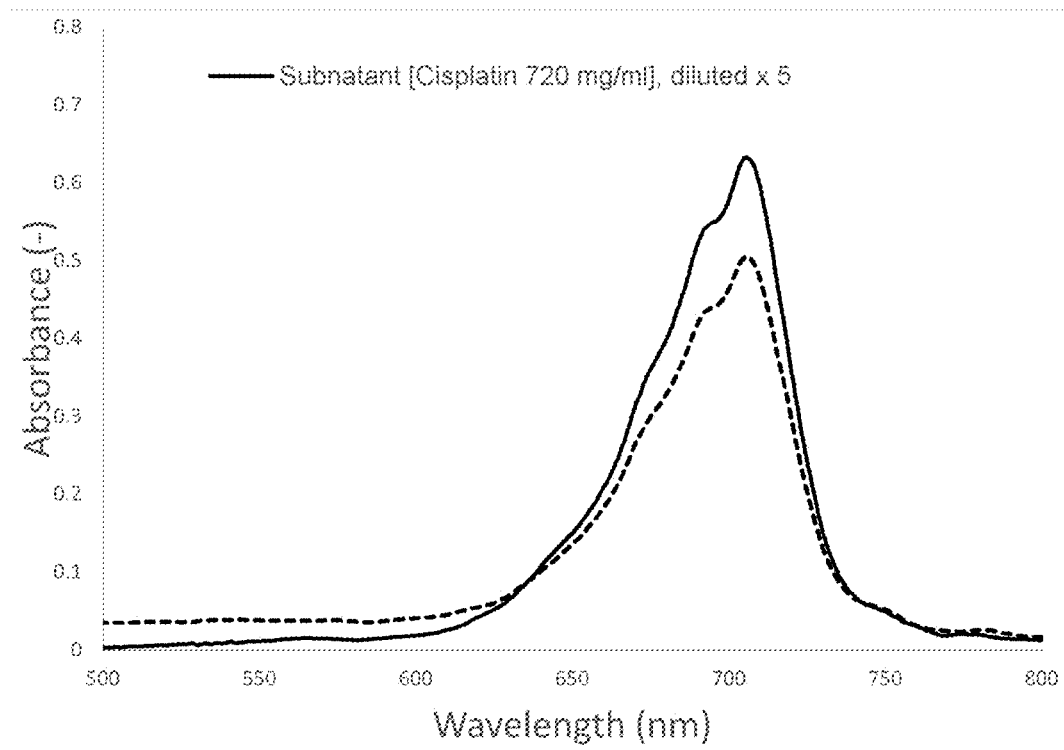
FIG. 14: Absorption spectrum of the subnatants of Examples 15 and 16 after treatment as described in the examples.
Figure 15:
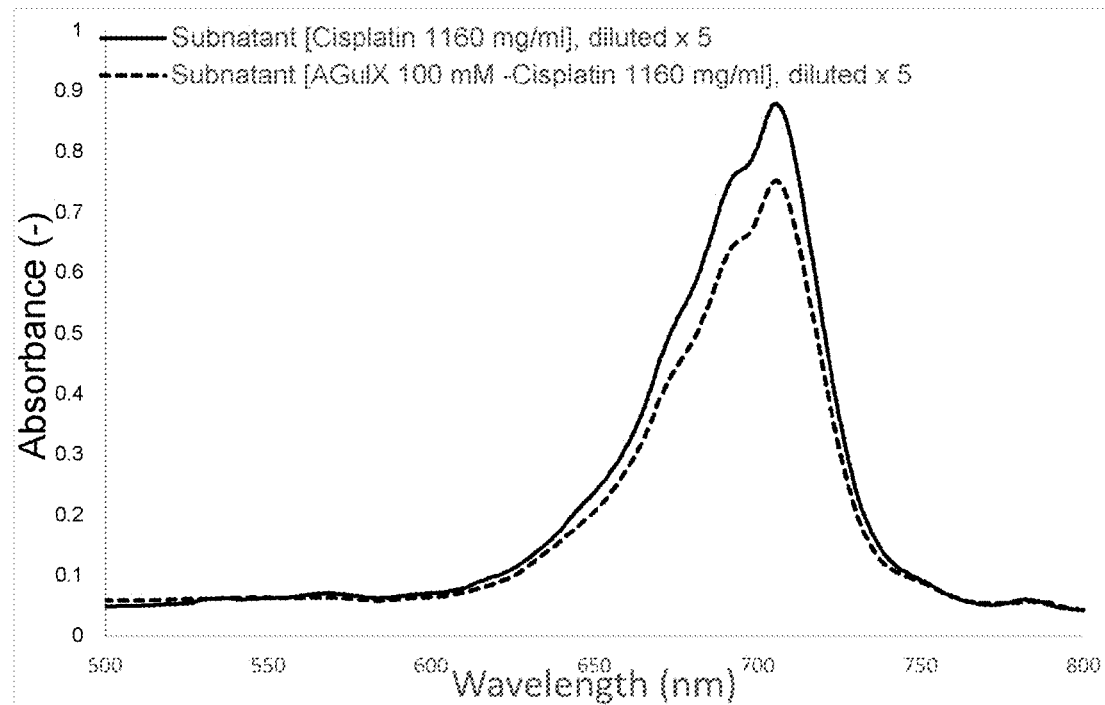
FIG. 15: Absorption spectrum of the subnatants of Examples 17 and 18 after treatment as described in the examples.
Figure 16:
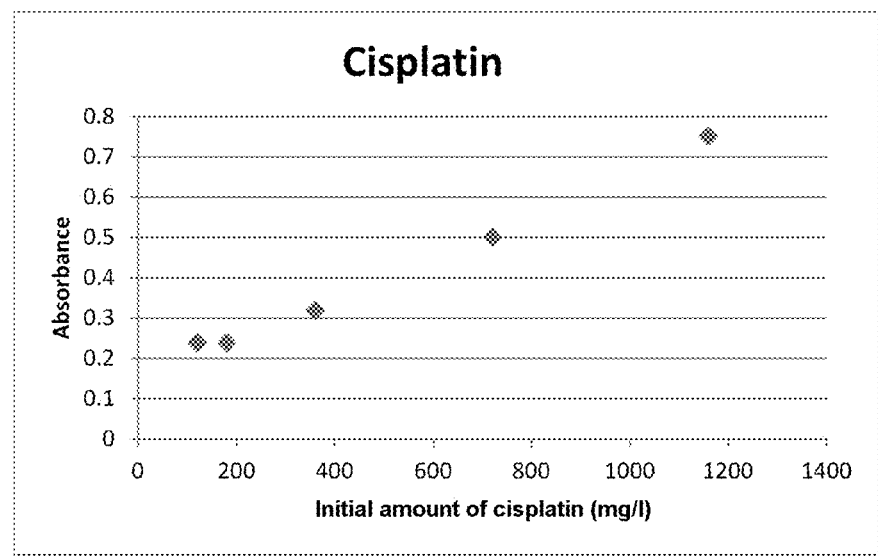
FIG. 16: Absorption values at 706 nm of the subnatants of the solutions of cisplatin in the presence of AGuIX® at 100 mM as a function of the amount of cisplatin introduced. The subnatants were subjected beforehand to a treatment as described in the examples in order to allow the detection of the cisplatin by absorption.

FIGS. 14 and 15 represent, respectively, the absorption spectra of the subnatants of the solutions of Examples 15 and 16, and of the solutions of Examples 17 and 18. These data show that the cisplatin adsorbs at the surface of the nanoparticles up to a concentration of approximately 240 mg·$L^{-1}$ (FIG. 16). Indeed, before this limiting concentration, the signal detected in the ODPA-treated subnatants, by UV/VIS spectrophotometry at 706 nm, is not modified.

For a solution of AGuIX® nanoparticles at 100 mM ([$Gd^{3+}$]) corresponding to 100 g/l of nanoparticles, a retention of the cisplatin is observed up to a minimum concentration of 240 mg/l, which corresponds to a load content by weight of greater than 2.4 mg/g of nanoparticles (FIG. 16).

Example 19

Nanoparticles based on polysiloxane and on free chelates for cisplatin delivery.

For the synthesis of these nanoparticles, 6.187 ml (26.17 mmol) of APTES are added to 90 ml of diethylene glycol. The solution is stirred for 1 h at ambient temperature before 10 g (17.45 mmol) of DOTAGA anhydride are added. The solution is left to stir for 5 days. At the end of this, 7.952 ml of TEOS (34.90 mmol) are added to the solution, which is stirred for 1 hour. 900 ml of ultrapure water are then added, before heating at 50° C. with stirring for 18 h. The solution is then concentrated to 200 ml on a Vivaflow cassette with membranes having a cut-off threshold of 5 kDa. The pH is adjusted to 2 by adding hydrochloric acid. The solution is purified by a factor of 50 by Vivaflow, before being neutralized to pH 7.4 by controlled addition of 1 M sodium hydroxide. The solution is filtered and then lyophilised. After redispersion in water, the nanoparticles have a hydrodynamic diameter of 5.2 nm.

50 μmol (DOTAGA) of silica nanoparticles (62.5 mg) were redispersed in 141 μl of ultrapure water in order to obtain a solution at 354 mM of DOTAGA and 443 mg/l. 3 mg of cisplatin are placed in a 2.5 ml flask. 1.2 ml of ultrapure water are added to the flask, which is stirred. Since cisplatin is not very soluble at ambient temperature, it is necessary to heat at 40° C. until it has completely dissolved. A solution containing 2.5 g/l of cisplatin is then obtained, and is protected from the light with aluminium. 229 μl of this solution are then added to the solution of silica nanoparticles, as are 130 μl of ultrapure water. The flask is stirred for 30 minutes in the dark. A solution containing 100 mM of free chelate (125 g/l of nanoparticles) and 1160 mg/l of cisplatin is thus obtained.

This solution is placed in a 3 kDa Vivaspin®, and a tangential filtration cycle is carried out so as to obtain a supernatant of 200 μl. The subnatant is analysed by UV-visible analysis. The cisplatin is detectable by UV/VIS absorption at a wavelength of 706 nm after reaction with ODPA. For the reaction with cisplatin, a solution of ODPA at 1.4 mg/ml and a phosphate buffer (pH 6.8) are prepared. The subnatant is diluted 5-fold. 140 μl of this solution are added to 200 μl of buffer and 100 μl of ODPA. This new solution is heated at 100° C. for 15 min. Once the reaction has finished and the temperature has returned to ambient temperature, 560 μl of DMF are added. The final solution is filtered and then analysed by UV-visible analysis.

Figure 17:
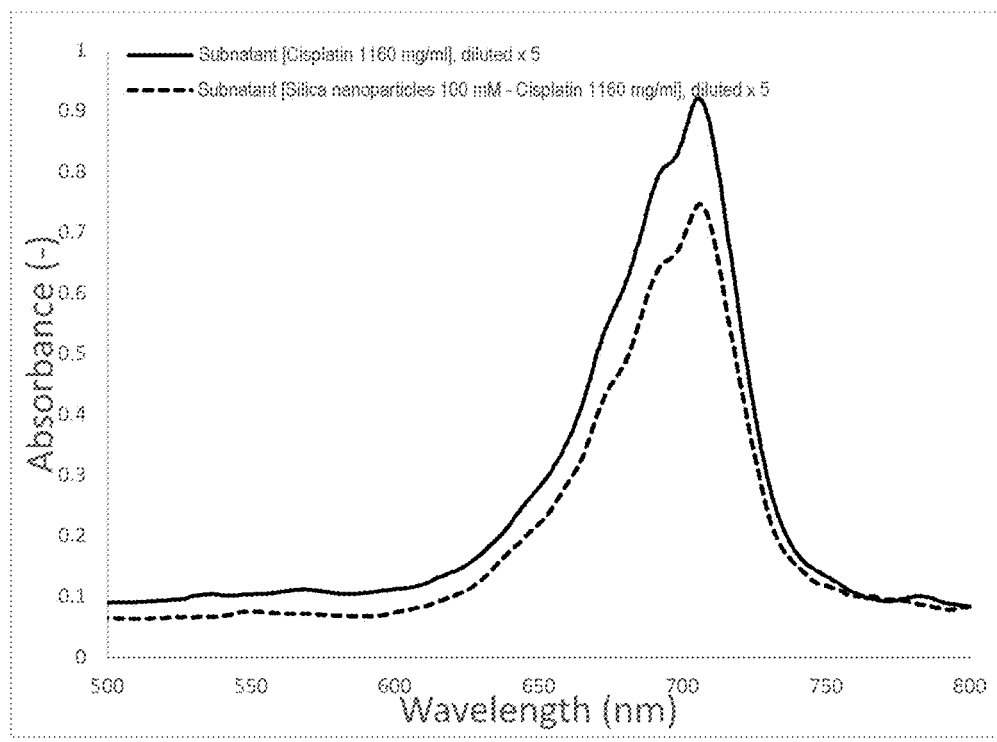
FIG. 17: Absorbance spectra of the subnatants of Examples 18 and 19 after treatment as described in the preceding examples.

FIG. 17 represents the absorption spectra of the subnatants of the solutions Examples 18 and 19. A weaker signal can be observed in the subnatants for the cisplatin added to the solution of silica nanoparticles. The signal at 706 nm of the two UV spectra makes it possible to estimate a retention of a cisplatin concentration of 260 mg/l for a solution of nanoparticles at 125 g/l, corresponding to a load content by weight of 2.1 mg/g of nanoparticles.

Example 20

Possibility of varying the load content by modifying the surface of the nanoparticles by chelation of bismuth ions.

The nanoparticles described in Example 19 are dispersed in water (283 mg, 227 μmol of DOTAGA) in order to have a DOTAGA concentration of approximately 200 mM. The pH of the solution is adjusted to 5.5 by adding NaOH. 817 μl of a solution of $BiCl_3$ at 250 mM in 6 M HCl are slowly added in 3 additions with stirring at a temperature of 70° C. to accelerate the complexation. Between each addition, the pH is readjusted to 5.5 by slowly adding a 10 M sodium hydroxide solution. The solution is then heated to 80° C. for 1 hour after the final addition. At the end of this, ultrapure water is added to reach a chelate concentration of 100 mM at a pH of 5.5. The solution is then heated at 80° C. for 18 h. The excess $Bi^{3+}$ is removed by tangential filtration, then the solution is neutralized to reach a pH of 7 by adding sodium hydroxide, before filtration on a 0.2 μm membrane and lyophilisation. After redispersion in the water, the nanoparticles have a hydrodynamic diameter of 6.0 nm.

30 μmol of AGuIX@DOTA@Bi ($Bi^{3+}$) (67.8 mg) were redispersed in 75 μl of ultrapure water in order to obtain a solution at 400 mM (904 g/L of nanoparticles). 3 mg of cisplatin are placed in a 2.5 ml flask. 1.2 ml of ultrapure water are added to the flask, which is stirred. Since cisplatin is not very soluble at ambient temperature, it is necessary to heat at 40° C. until it is completely dissolved. A solution containing 2.5 g/l of cisplatin is then obtained, and is protected from the light with aluminium. 118 μl of this solution are then added to the solution of AGuIX@DOTA@Bi, as are 107 μl of ultrapure water. The flask is stirred for 30 minutes in the dark. A solution containing 100 mM of bismuth (226 g/l of nanoparticles) and 1000 mg/l of cisplatin is thus obtained.

This solution is placed in a 3 kDa Vivaspin®, and a tangential filtration cycle is carried out so as to obtain a supernatant of 80 μl. The subnatant is analysed by UV-visible analysis. The cisplatin is detectable by UV/VIS absorption at a wavelength of 706 nm after reaction with ODPA. For the reaction with cisplatin, a solution of ODPA at 1.4 mg/ml and a phosphate buffer (pH 6.8) are prepared. The subnatant is diluted 5-fold. 140 μl of this concentration are added to 200 μl of buffer and 100 μl of ODPA. This new solution is heated at 100° C. for 15 min. Once the reaction has finished and the temperature has returned to ambient temperature, 560 μl of DMF are added. The final solution is filtered and then analysed by UV-visible analysis.

Results of Examples 18 and 20

Figure 18:
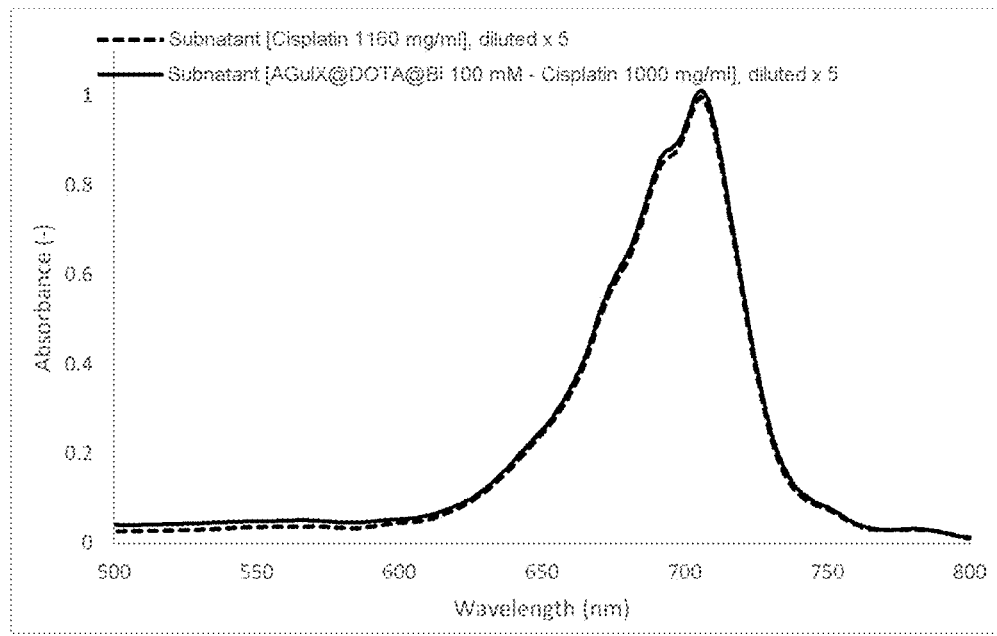
FIG. 18: Absorbance spectrum of the subnatants of Examples 18 and 20 after treatment as described in the examples.

FIG. 18 represents the absorption spectra of the subnatants of the solutions of Examples 18 and 20.

As shown in FIG. 18, the chelation of bismuth at the surface of the nanoparticles leads to a non-retention of the cisplatin at the surface of the nanoparticles, proving that changes regarding the number of metal elements chelated at the surface of the nanoparticles make it possible to vary the load content of the nanoparticles.

The invention claimed is:

1. A nanovector for the delivery of an active substance in a human being, wherein said nanovector comprises a nanoparticle on the surface of which the active substance is bonded by physisorption, said nanoparticle is a polysiloxane-based nanoparticle with a mean diameter of less than 10 nm, the active substance is chosen from organic molecules which have a molar mass of between 2% and 40% of the total molar mass of said nanoparticle, and said nanoparticle comprises:
   a. polysiloxanes, with a weight ratio of silicon of at least 8% of the total weight of the nanoparticle,
   b. a chelating agent grafted onto the nanoparticle, wherein the chelating agent which is grafted onto the nanoparticle is selected from DOTA, DTPA, EDTA, EGTA, BAPTA, NOTA, DOTAGA and DTPABA or a mixture thereof, and
   c. optionally, a metal element, said metal element being complexed to the chelating agent.

2. The nanovector according to claim 1, wherein the load content, expressed in milligrams of active substance per gram of nanovector, is greater than 0.5 mg/g.

3. The nanovector according to claim 1, wherein the nanoparticle is of formula (I) below:

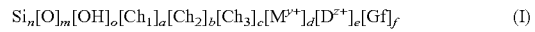

in which:
   n is between 20 and 5000,
   m is greater than n and less than 4 n,
   o is between 0 and 2 n,
   $Ch_1$, $Ch_2$ and $Ch_3$ are chelating agents, which may be identical or different, bonded to the Si atoms of the polysiloxanes by an Si—C covalent bond; a, b and c are integers between 0 and n and a+b+c is less than or equal to n, M$^{y+}$ and D$^{z+}$ are metal cations, which may be identical to or different from one another, with y and z=1 to 6; d and e are integers between 0 and a+b+c, and d+e is less than or equal to a+b+c, Gf is a targeting graft, which may be identical to or different from one another, each bonded to the Si by an Si—C bond and resulting from the grafting of a targeting molecule allowing the targeting of the nanoparticle to biological tissues of interest, and f is an integer between 0 and n.

4. The nanovector according to claim 1, wherein the nanovector comprises a metal element chosen from elements with a high atomic number Z.

5. The nanovector according to claim 1, wherein said nanoparticle is a polysiloxane-based nanoparticle with a mean diameter of between 1 and 5 nm, comprising gadolinium complexed to the chelating agent obtained by grafting of DOTAGA onto the nanoparticle.

6. The nanovector according to claim 1, wherein the active substance is chosen from small organic molecules having a molar mass of less than 5000.

7. The nanovector according to claim 1, wherein said nanoparticle comprises a targeting agent covalently grafted to the polysiloxanes and allowing active targeting of biological zones of interest.

8. The nanovector according to claim 1, wherein said active substance is chosen from anti-cancer substances.

9. The nanovector according to claim 8, wherein said anti-cancer substance is chosen from the following substances: actinomycin, all-trans retinoic acid, azacitidine, azathioprine, bleomycin, bortezomib, carboplatin, capecitabine, cisplatin, chlorambucil, cyclophosphamide, cytarabin, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vemurafenib, vinblastine, vincristine, vindesine, lenalidomide, ibrutinib, abiraterone, erlotinib, everolimus, nilotinib, sunitinib, sorafenib, goserelin, nedaplatin, laboplatin, TATE peptide and heptaplatin, or a mixture thereof.

10. The nanovector according to claim 1, wherein the nanoparticle comprises a chelate of an element with an atomic number greater than 40, having a radiosensitizing effect.

11. The nanovector according to claim 1, wherein the nanoparticle comprises a metal element chelate, said metal element being chosen for use in imaging by magnetic resonance imaging, scans or scintigraphy.

12. The nanovector according to claim 1 wherein said nanoparticle comprises:
a. polysiloxanes, with a weight ratio of silicon between 8% and 50% of the total weight of the nanoparticle,
b. the chelating agent in a proportion of between 5 and 100 per nanoparticle, and
c. optionally, the metal element in a proportion of between 5 and 100 per nanoparticle, said metal element being complexed to the chelating agent.

13. The nanovector according to claim 1, wherein the load content, expressed in milligrams of active substance per gram of nanovector, is between 1 mg/g and 100 mg/g.

14. The nanovector according to claim 1, wherein the nanovector comprises a metal element chosen from elements with a high atomic number Z chosen from gadolinium, bismuth or a mixture thereof.

15. The nanovector according to claim 3, wherein the nanovector comprises a metal element chosen from elements with a high atomic number Z chosen from gadolinium, bismuth or a mixture thereof.

16. An injectable pharmaceutical solution comprising a nanovector according to claim 1, and at least one pharmaceutically acceptable excipient.

17. The injectable pharmaceutical solution according to claim 16, wherein the nanovector comprises an element with a high atomic number Z greater than 40, and wherein said high-Z element is at a concentration between 10 and 200 mM in said solution.

18. The injectable pharmaceutical solution according to claim 16, wherein the active substance of the nanovector is chosen from doxorubicin, cisplatin and the TATE peptide.

19. The injectable pharmaceutical solution according to claim 16, wherein the injectable pharmaceutical solution is directly obtained by means of a method for preparing a nanovector for the delivery of an active substance in a human being, said method comprising mixing two solutions that can be administered in a human being:
a. a first solution comprising a nanoparticle, said nanoparticle being a polysiloxane-based nanoparticle having a mean diameter of less than 10 nm, and
b. a second solution comprising an active substance or a mixture of active substances chosen from organic molecules, under concentration ratio, pH and temperature conditions which allow an interaction by physisorption of the active substance or mixture of active substances at the surface of said nanoparticle.

20. A method for preparing a nanovector according to claim 1, said method comprising mixing two solutions:
a. a first solution comprising a nanoparticle, said nanoparticle being a polysiloxane-based nanoparticle having a mean diameter of less than 10 nm, wherein said nanoparticle comprises polysiloxanes with a weight ratio of silicon of at least 8% of the total weight of the nanoparticle and a chelating agent grafted onto the nanoparticle, wherein the chelating agent which is grafted onto the nanoparticle is selected from DOTA, DTPA, EDTA, EGTA, BAPTA, NOTA, DOTAGA and DTPABA or a mixture thereof, and
b. a second solution comprising an active substance chosen from organic molecules having a molecular weight of between 2% and 40% of the molecular weight of said nanoparticle, under concentration ratio, pH and temperature conditions which allow an interaction by physisorption of the active substance at the surface of said nanoparticle.

21. The method according to claim 20, wherein the [active substance in the second solution]:[nanoparticle in the first solution] concentration ratio by weight is greater than 0.5 mg/g.

22. The method according to claim 20 wherein the active substance is chosen from small organic molecules with a molar mass of less than 5000 g·mol$^{-1}$.

23. The method according to claim 20, wherein the active substances are substance is chosen from one of the following anti-cancer substances: actinomycin, all-trans retinoic acid, azacitidine, azathioprine, bleomycin, bortezomib, carboplatin, capecitabine, cisplatin, chlorambucil, cyclophosphamide, cytarabin, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vemurafenib, vinblastine, vincristine, vindesine, lenalidomide, ibrutinib, abiraterone, erlotinib, everolimus, nilotinib, sunitinib, sorafenib, goserelin, nedaplatin, laboplatin and heptaplatin, or a mixture thereof.

24. The method according to claim 20, comprising a step of purifying the nanovector obtained after mixing of the solutions, so as to remove the possible active substance that has remained free in solution, and recovering the nanovector comprising the nanoparticle, at the surface of which the active substance is bonded by physisorption.

\* \* \* \* \*